US012784868B2

(12) United States Patent
Yokoyama et al.

(10) Patent No.: US 12,784,868 B2
(45) Date of Patent: Nov. 3, 2026

(54) GENOTYPE ANALYSIS DEVICE AND METHOD

(71) Applicant: HITACHI HIGH-TECH CORPORATION, Tokyo (JP)

(72) Inventors: Toru Yokoyama, Tokyo (JP); Michiru Fujioka, Tokyo (JP); Ayaka Okuno, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 1444 days.

(21) Appl. No.: 17/432,170

(22) PCT Filed: Feb. 14, 2020

(86) PCT No.: PCT/JP2020/005718
§ 371 (c)(1),
(2) Date: Aug. 19, 2021

(87) PCT Pub. No.: WO2020/179405
PCT Pub. Date: Sep. 10, 2020

(65) Prior Publication Data

US 2022/0189577 A1 Jun. 16, 2022

(30) Foreign Application Priority Data

Mar. 5, 2019 (JP) ................................ 2019-039262

(51) Int. Cl.
*G16B 5/00* (2019.01)
*C12Q 1/6809* (2018.01)
*G16B 40/20* (2019.01)

(52) U.S. Cl.
CPC ............ *G16B 5/00* (2019.02); *C12Q 1/6809* (2013.01); *G16B 40/20* (2019.02)

(58) Field of Classification Search
CPC .......... G16B 5/00; G16B 40/20; G16B 40/10; C12Q 1/6809; C12M 1/00; C12M 1/34; C12N 15/09
See application file for complete search history.

(56) References Cited

U.S. PATENT DOCUMENTS 9,605,300 B2 * 3/2017 Yokoyama ............ G16B 20/20
2002/0147549 A1 10/2002 Yoshida et al.
(Continued)

FOREIGN PATENT DOCUMENTS

JP 2002-005886 A 1/2002
JP 2002-350401 A 12/2002
(Continued)

OTHER PUBLICATIONS

Novo et al. (Current advances and challenges in microfluidic free-flow electrophoresis—A critical review, Analytica Chimica Acta, vol. 991, Oct. 23, 2017, pp. 9-29) (Year: 2017).*
(Continued)

*Primary Examiner* — G. Steven Vanni
*Assistant Examiner* — Ghazal Sabour
(74) *Attorney, Agent, or Firm* — Volpe Koenig

(57) ABSTRACT

A genotype analysis device includes an electrophoresis device and a data analysis device. A mobility model management unit including an environment information receiving unit, a prediction model storage unit, and a mobility prediction unit is provided in an STR analysis unit of the data analysis device. The mobility prediction unit generates a prediction model for predicting a correction amount of a standard base length of an allele, based upon an environmental condition at the time of electrophoresis received by the environmental information receiving unit and an electrophoresis result of an allelic ladder. A base length of the
(Continued)

allele is corrected from the environmental condition without using the allelic ladder by using the prediction model.

17 Claims, 20 Drawing Sheets

(56) References Cited

U.S. PATENT DOCUMENTS

| | | | | |
|---|---|---|---|---|
| 2007/0044541 | A1* | 3/2007 | Ikuta | G01N 27/44726 73/53.01 |
| 2007/0256935 | A1* | 11/2007 | Sugimoto | G01N 27/447 204/451 |
| 2015/0337360 | A1 | 11/2015 | Yokoyama et al. | |
| 2019/0019290 | A1* | 1/2019 | Tan | G06T 7/0014 |
| 2019/0383742 | A1 | 12/2019 | Anazawa | |

FOREIGN PATENT DOCUMENTS

| | | | |
|---|---|---|---|
| JP | 2004-325191 | A | 11/2004 |
| JP | 6087128 | B2 | 3/2017 |
| WO | 2006/022283 | A1 | 3/2006 |
| WO | 2014/097888 | A1 | 6/2014 |
| WO | 2018/150559 | A1 | 8/2018 |

OTHER PUBLICATIONS

Holland et al. (GeneMarker® HID: A Reliable Software Tool for the Analysis of Forensic STR Data, Jan. 3, 2011, American Academy of Forensic Sciences, pp. 29-35) (Year: 2011).*
Raschka (Model Evaluation, Model Selection, and Algorithm Selection in Machine Learning, University of Wisconsin—Madison Department of Statistics Nov. 2018, pp. 1-49) (Year: 2018).*
Examination Report dated Nov. 18, 2022 for UK Patent Application No. 2112209.8.

* cited by examiner

FIG. 10

113

| Dye | Locus | Allele | Length | Min | Max |
|---|---|---|---|---|---|
| 6FAM | D10S1248 | 8 | 77 | -0.5 | 0.5 |
| | | 9 | 81 | -0.5 | 0.5 |
| | | 10 | 85 | -0.5 | 0.5 |
| | | 11 | 89 | -0.5 | 0.5 |
| | | 12 | 93 | -0.5 | 0.5 |
| | | 13 | 97 | -0.5 | 0.5 |
| | | 14 | 101 | -0.5 | 0.5 |
| | | 15 | 105 | -0.5 | 0.5 |
| | | 16 | 109 | -0.5 | 0.5 |
| | | 17 | 113 | -0.5 | 0.5 |
| | | 18 | 117 | -0.5 | 0.5 |
| NED | D22S1045 | 8 | 80 | -0.5 | 0.5 |
| | | 9 | 83 | -0.5 | 0.5 |
| | | 10 | 86 | -0.5 | 0.5 |
| | | ... | ... | ... | ... |

114

| Dye | Locus | Allele | Length | Offset | Min | Max |
|---|---|---|---|---|---|---|
| 6FAM | D10S1248 | 8 | 77 | 1 | -0.5 | 0.5 |
| | | 9 | 81 | 1 | -0.5 | 0.5 |
| | | 10 | 85 | 1 | -0.5 | 0.5 |
| | | 11 | 89 | 1 | -0.5 | 0.5 |
| | | 12 | 93 | 1.1 | -0.5 | 0.5 |
| | | 13 | 97 | 1.1 | -0.5 | 0.5 |
| | | 14 | 101 | 1.1 | -0.5 | 0.5 |
| | | 15 | 105 | 1.1 | -0.5 | 0.5 |
| | | 16 | 109 | 1.1 | -0.5 | 0.5 |
| | | 17 | 113 | 1.2 | -0.5 | 0.5 |
| | | 18 | 117 | 1.2 | -0.5 | 0.5 |
| NED | D22S1045 | 8 | 80 | 1.5 | -0.5 | 0.5 |
| | | 9 | 83 | 1.5 | -0.5 | 0.5 |
| | | 10 | 86 | 1.5 | -0.5 | 0.5 |
| | | ... | ... | | ... | ... |

115

| Dye | Locus | Allele | Length | Offset | Offset2 | Offset3 | Min | Max |
|---|---|---|---|---|---|---|---|---|
| 6FAM | D10S1248 | 8 | 77 | 1 | -0.2 | -0.3 | -0.5 | 0.5 |
| | | 9 | 81 | 1 | -0.2 | -0.2 | -0.5 | 0.5 |
| | | 10 | 85 | 1 | -0.1 | -0.2 | -0.5 | 0.5 |
| | | 11 | 89 | 1 | -0.1 | -0.1 | -0.5 | 0.5 |
| | | 12 | 93 | 1.1 | 0.1 | 0 | -0.5 | 0.5 |
| | | 13 | 97 | 1.1 | 0.1 | 0.1 | -0.5 | 0.5 |
| | | 14 | 101 | 1.1 | 0.1 | 0.1 | -0.5 | 0.5 |
| | | 15 | 105 | 1.1 | 0.1 | 0.2 | -0.5 | 0.5 |
| | | 16 | 109 | 1.1 | 0.2 | 0.2 | -0.5 | 0.5 |
| | | 17 | 113 | 1.2 | 0.2 | 0.3 | -0.5 | 0.5 |
| | | 18 | 117 | 1.2 | 0.3 | 0.4 | -0.5 | 0.5 |
| NED | D22S1045 | 8 | 80 | 1.5 | -0.6 | -0.8 | -0.5 | 0.5 |
| | | 9 | 83 | 1.5 | -0.5 | -0.7 | -0.5 | 0.5 |
| | | 10 | 86 | 1.5 | -0.5 | -0.6 | -0.5 | 0.5 |
| | | ... | ... | ... | ... | ... | ... | ... |

| Date | Data |
|---|---|
| 20180112 | ··· |
| 20180124 | ··· |
| 20180205 | ··· |
| ··· | ··· |
| ··· | ··· |

118

| Dye | Locus | Allele | Length | Offset | Temp. | Current |
|---|---|---|---|---|---|---|
| 6FAM | D10S1248 | 8 | 77 | -0.2 | 13 | 0.2 |
| | | 9 | 81 | -0.2 | 13 | 0.2 |
| | | 10 | 85 | -0.1 | 13 | 0.2 |
| | | 11 | 89 | -0.1 | 13 | 0.2 |
| | | 12 | 93 | 0.1 | 13 | 0.3 |
| | | 13 | 97 | 0.1 | 13 | 0.3 |
| | | 14 | 101 | 0.1 | 13 | 0.3 |
| | | 15 | 105 | 0.1 | 13 | 0.3 |
| | | 16 | 109 | 0.2 | 13 | 0.3 |
| | | 17 | 113 | 0.2 | 13 | 0.3 |
| | | 18 | 117 | 0.3 | 13 | 0.3 |
| NED | D22S1045 | 8 | 80 | -0.6 | 13 | 0.2 |
| | | 9 | 83 | -0.5 | 13 | 0.2 |
| | | 10 | 86 | -0.5 | 13 | 0.2 |
| | | ... | ... | ... | ... | ... |

FIG. 23A

116

| Dye | Length | Min | Max |
|---|---|---|---|
| 6FAM | 100 | -0.5 | 0.5 |
| | 200 | -0.5 | 0.5 |
| | 300 | -0.5 | 0.5 |
| | 400 | -0.5 | 0.5 |
| VIC | 140 | -0.5 | 0.5 |
| | 240 | -0.5 | 0.5 |
| | 340 | -0.5 | 0.5 |
| | 440 | -0.5 | 0.5 |
| NED | 160 | -0.5 | 0.5 |
| | 260 | -0.5 | 0.5 |
| | 360 | -0.5 | 0.5 |
| | 460 | -0.5 | 0.5 |
| PET | 180 | -0.5 | 0.5 |
| | 280 | -0.5 | 0.5 |
| | 380 | -0.5 | 0.5 |
| | 480 | -0.5 | 0.5 |

FIG. 23B

117

| Dye | Length | Offset | Min | Max |
|---|---|---|---|---|
| 6FAM | 100 | -0.1 | -0.5 | 0.5 |
| | 200 | 0 | -0.5 | 0.5 |
| | 300 | 0.2 | -0.5 | 0.5 |
| | 400 | 0.4 | -0.5 | 0.5 |
| VIC | 140 | -0.1 | -0.5 | 0.5 |
| | 240 | 0.5 | -0.5 | 0.5 |
| | 340 | 0.6 | -0.5 | 0.5 |
| | 440 | 0.6 | -0.5 | 0.5 |
| NED | 160 | 0.1 | -0.5 | 0.5 |
| | 260 | 0.3 | -0.5 | 0.5 |
| | 360 | 0.6 | -0.5 | 0.5 |
| | 460 | 0.8 | -0.5 | 0.5 |
| PET | 180 | -0.3 | -0.5 | 0.5 |
| | 280 | 0.1 | -0.5 | 0.5 |
| | 380 | 0.2 | -0.5 | 0.5 |
| | 480 | 0.4 | -0.5 | 0.5 |

GENOTYPE ANALYSIS DEVICE AND METHOD

BACKGROUND OF THE INVENTION

1. Field of the Invention

The present invention relates to a genotype analysis device using electrophoresis and a genotype analysis method.

2. Description of Related Art

A DNA test by analysis of deoxyribonucleic acid (DNA) polymorphism is currently widely performed for a criminal investigation, determination of a blood relationship, or the like. DNAs of organisms of the same species have almost similar base sequences, but in some places, the DNAs thereof have different base sequences. Such diversity seen in the base sequence on DNA between individuals is called DNA polymorphism, which is involved in formation of individual differences at a gene level.

One of the forms of the DNA polymorphism includes Short Tandem Repeat (STR) or microsatellite. The STR is a characteristic sequence pattern in which a short sequence having a length of about 2 to 7 bases is repeated several to several tens of times, and it is known that the number of repetitions varies depending on an individual. Analyzing a combination of the number of repetitions of the STR at a locus of a specific gene is referred to as STR analysis.

The DNA test for the purpose of criminal investigation or the like uses the STR analysis using a property that the combination of the number of repetitions of the STR is different between individuals. At the Federal Bureau of Investigation (FBI) and the International Criminal Police Organization (ICPO), the locus of STR used for the DNA test is defined as DNA markers of 10 to 10 or more, and a pattern of the number of repetitions of these STR sequences is analyzed. Since a difference in the number of repetitions of the STR occurs due to a difference in alleles (allelomorph), hereinafter, the number of repetitions of the STR in each DNA marker will be referred to as an allele.

Polymerase Chain Reaction (PCR) is performed to extract a certain amount of DNA at an STR portion to be used as the DNA marker. The PCR is a technology of obtaining a certain amount of target DNA samples by specifying a certain base sequence referred to as a primer sequence at opposite ends of the target DNA, and by repeatedly amplifying only a DNA fragment interposed between the primer sequences.

Electrophoresis is performed to measure a fragment length of the target DNA fragment obtained by the PCR. The electrophoresis is a method for separating the DNA fragment using a fact that a migration speed in a charged migration path is different depending on the length of the DNA fragment, and as the DNA fragment is longer, the migration speed becomes smaller. As a method of the electrophoresis, capillary electrophoresis using a capillary as a migration path is widely used in recent years.

In the capillary electrophoresis, a thin tube referred to as the capillary is filled with a migration medium such as gel or the like, and the DNA fragment of the sample is caused to migrate in the capillary. Next, the length of the DNA fragment is examined by measuring the time required for the sample to complete the electrophoresis for a certain distance, usually from one end of the capillary to the other end thereof. Each sample, that is, each DNA fragment is labeled with a fluorescent dye and an optical detector disposed at an end portion of the capillary detects a fluorescence signal of the electrophoresed sample.

It is known that the migration speed of the DNA fragment fluctuates depending on environments such as a migration medium, a reagent performance, a device temperature, a migration voltage value, or the like. When the migration speed changes, a size of the measured DNA fragment varies, such that the allele cannot be accurately identified. Therefore, a standard reagent referred to as an allelic ladder is generally used for the purpose of accurately identifying the allele with respect to the fluctuation in the migration speed. The allelic ladder is, as will be described later, is an artificial sample containing a plurality of alleles that may commonly be contained in the DNA marker, and can absorb the fluctuation in the migration speed and can fine-tune a correspondence relationship between the allele and the DNA fragment length.

Normally, the allelic ladder is provided by a reagent manufacturer as a reagent kit for the DNA test. As time goes by, the fluctuation in the migration speed caused by an environmental change is accumulated, such that in the STR analysis, it is recommended to use the allelic ladder at a constant frequency.

SUMMARY OF THE INVENTION

However, when the fluctuation in the migration speed is greater than the fluctuation expected in a recommended frequency of a related art, there is a problem that the fluctuation in the migration speed cannot be absorbed such that the DNA fragment size cannot be measured correctly.

On the contrary, even though a period of the recommended frequency passes, and when the fluctuation in the migration speed is small, there is also a problem that the allelic ladder is unnecessarily consumed such that run cost increases. Particularly, in a genetic testing device having only one capillary, the sample to be measured and the allelic ladder cannot be electrophoresed in different capillaries at the same time. In order to use the allelic ladder in the genetic testing device, it is required to perform the electrophoresis two times, such that the analysis becomes complicated.

The present invention has been made in consideration of the above-described circumferences, and an object thereof is to provide a genotype analysis device and a genotype analysis method in which a frequency of using an allelic ladder can be reduced such that analysis cost of STR analysis can be reduced.

In order to solve the above-described problem, the present invention provides a genotype analysis device including an electrophoresis device that obtains a spectrum by electrophoresis, and a data analysis device that obtains a base length of DNA based upon the spectrum and analyzes a genotype with reference to a standard base length, in which the data analysis device includes a mobility model management unit that predicts a correspondence between the standard base length and the measured base length of DNA based upon environmental information in the electrophoresis.

In order to solve the above-described problem, the present invention provides a genotype analysis method using a data analysis device, in which the data analysis device predicts a correspondence between a standard base length and a measured base length of DNA obtained based upon a spectrum obtained by electrophoresis, based upon environmental information in the electrophoresis.

According to the present invention, a frequency of using an allelic ladder can be reduced such that STR analysis can be implemented at low cost.

BRIEF DESCRIPTION OF THE DRAWINGS

FIG. 10 is a diagram illustrating a correspondence relationship table (Look Up Table: LUT) according to the first embodiment;

FIGS. 23A and 23B are diagrams illustrating an example of positive control information according to the third embodiment.

DESCRIPTION OF EMBODIMENTS

Hereinafter, various embodiments of a genotype analysis device and a genotype analysis method for predicting a correction amount of a base length of DNA during electrophoresis of an actual sample based upon environmental information will be sequentially described with reference to the accompanying drawings. However, it should be noted that each embodiment is only one example for implementing the present invention and does not limit the technical scope of the present invention. A common configuration in each drawing will be denoted by the same reference sign.

First Embodiment

A first embodiment is an embodiment of a genotype analysis device including an electrophoresis device that obtains a spectrum by electrophoresis, and a data analysis device that obtains a base length of DNA based upon the spectrum and analyzes a genotype with reference to a standard base length, wherein the data analysis device includes a mobility model management unit that predicts a correspondence between the standard base length and the measured base length of DNA based upon environmental information in the electrophoresis. The present embodiment is an embodiment of a genotype analysis method using a data analysis device, in which the data analysis device predicts a correspondence between a standard base length and a measured base length of DNA obtained based upon a spectrum obtained by electrophoresis, based upon environmental information in the electrophoresis.

Figure 1:
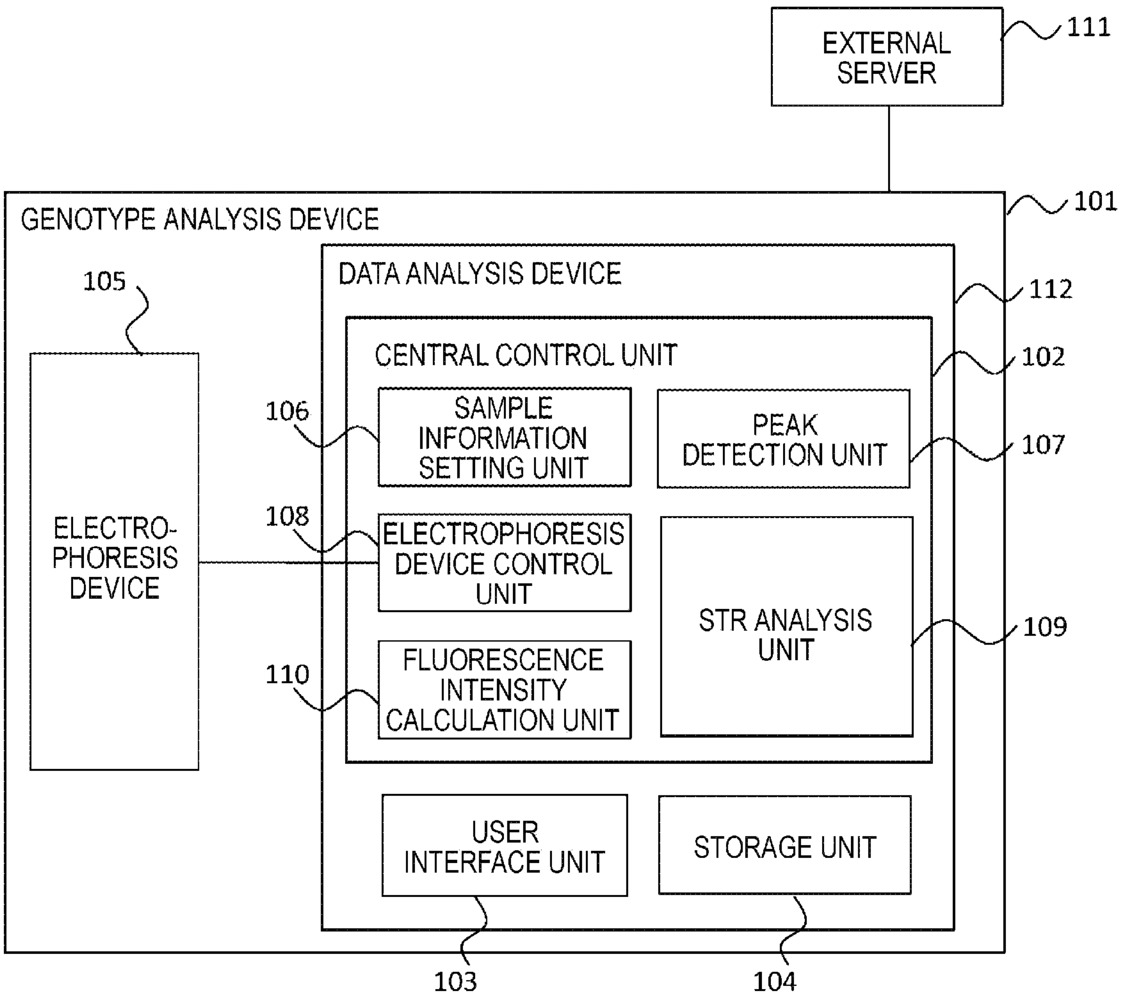
FIG. 1 is a diagram illustrating a schematic configuration of a genotype analysis device according to a first embodiment.

FIG. 1 illustrates a configuration of the genotype analysis device of the first embodiment. A genotype analysis device 101 includes a data analysis device 112 and an electrophoresis device 105. The data analysis device 112 includes: a central control unit 102 that performs control of electrophoresis, a data process, or the like; a user interface unit 103 that uses a display unit to provide information such as a list of applicable prediction models which will be described later to a user, and that uses an input unit to input information from the user; and a storage unit 104 that stores data and device setting information. When the data analysis device 112 is connected to an external server 111 via a network, various data such as prediction model data or the like can be transmitted and received therebetween.

Figure 8:
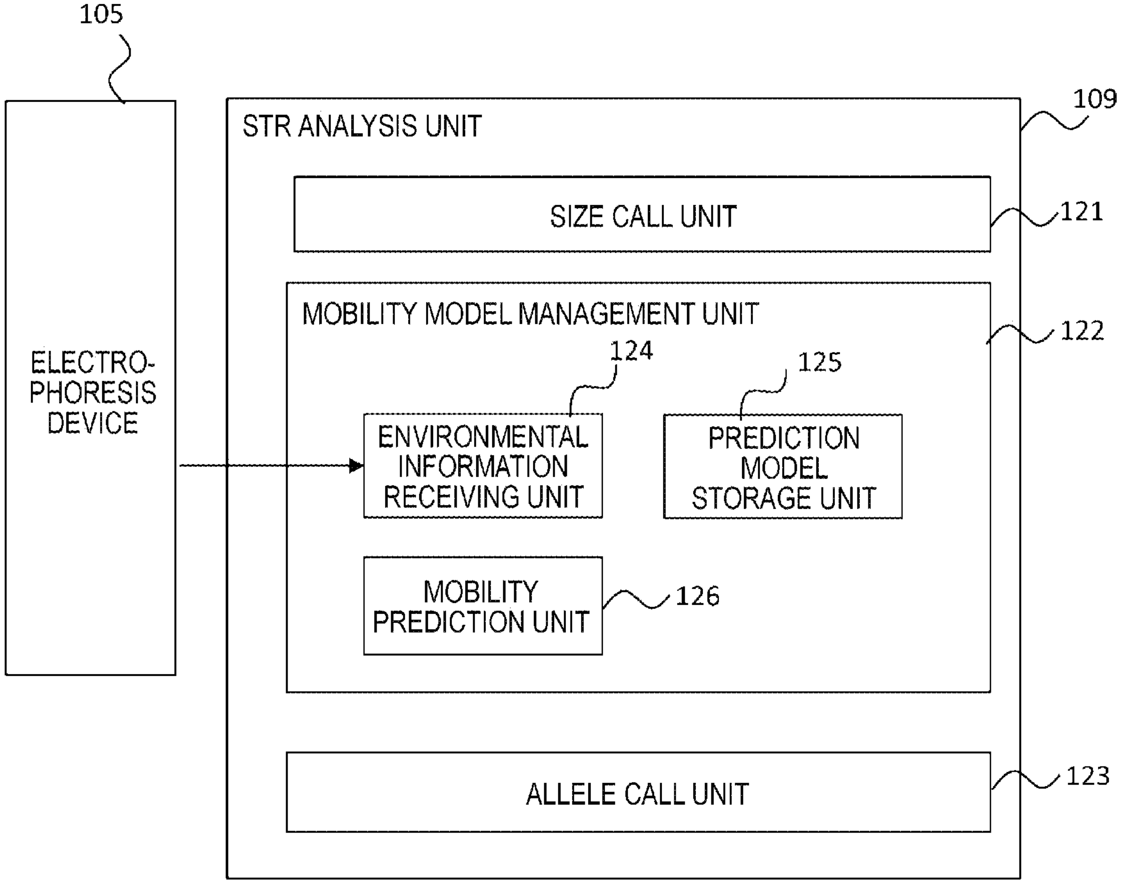
FIG. 8 is a diagram illustrating a schematic configuration of an STR analysis unit according to the first embodiment.

The central control unit 102 includes a sample information setting unit 106, an electrophoresis device control unit 108, a fluorescence intensity calculation unit 110, a peak detection unit 107, and an STR analysis unit 109. A block configuration in the STR analysis unit 109 is illustrated in FIG. 8. The STR analysis unit 109 includes a Size Call unit 121, a mobility model management unit 122, and an Allele Call unit 123. The mobility model management unit 122 includes an environmental information receiving unit 124, a prediction model storage unit 125, and a mobility prediction unit 126. Respective functions thereof will be described later.

Figure 2:
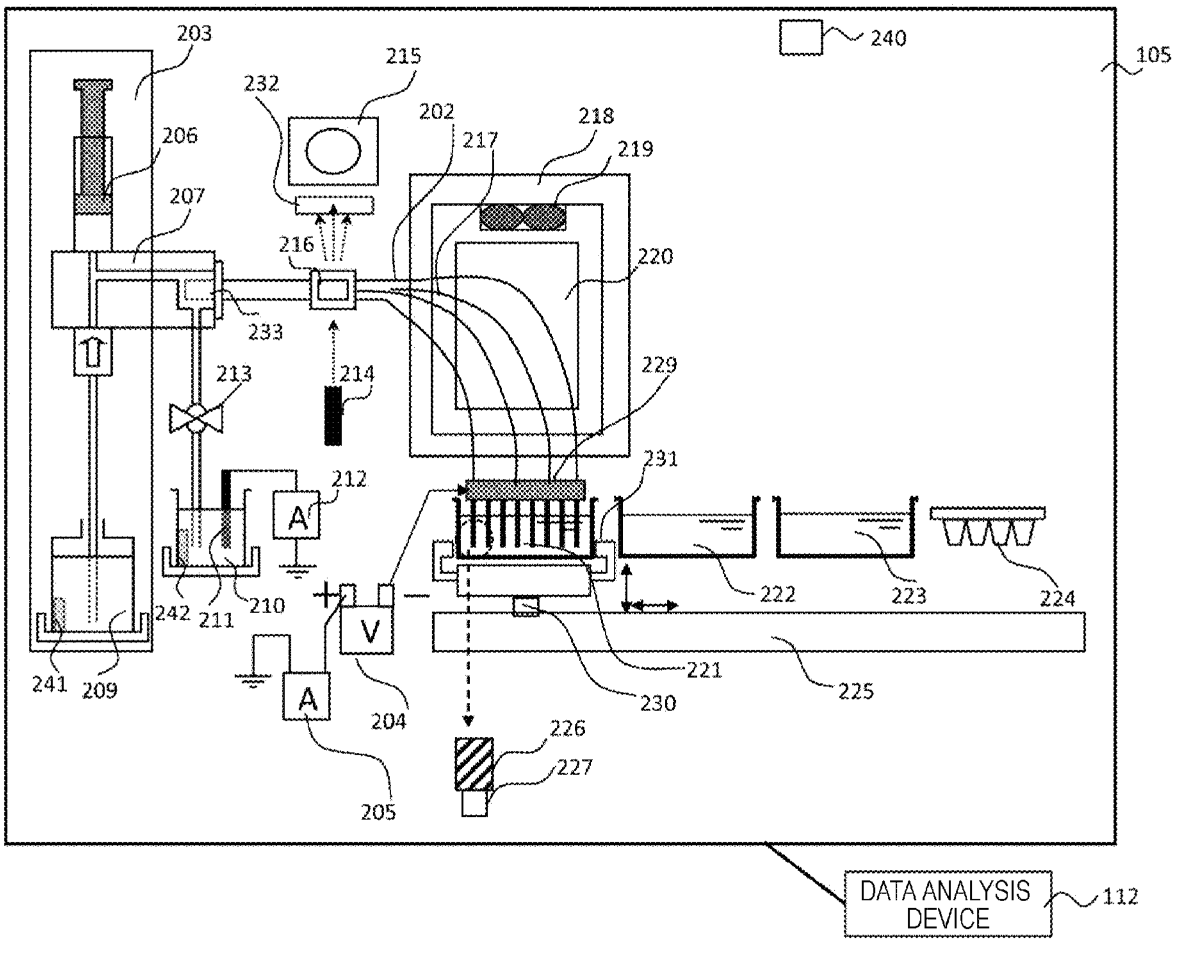
FIG. 2 is a diagram illustrating a schematic configuration of an electrophoresis device according to the first embodiment.

FIG. 2 is a schematic diagram of the electrophoresis device 105. A configuration of the electrophoresis device 105 will be described with reference to FIG. 2. The electrophoresis device 105 includes: a detection unit 216 for optically detecting a sample; a constant temperature bath 218 for keeping the capillary at a constant temperature; a conveyor 225 for conveying various containers to a capillary cathode end; a high voltage power supply 204 for applying a high voltage to the capillary; a first ammeter 205 for detecting a current emitted from the high voltage power supply; a second ammeter 212 for detecting a current flowing through an anode side electrode 211; a capillary array 217 configured with one or a plurality of capillaries 202; and a pump mechanism 203 for injecting a polymer into the capillary.

The capillary array 217 is a replacement member including a plurality of (for example, eight) capillaries, and includes a load header 229, the detection unit 216, and a capillary head 233. When damage and deterioration in quality are observed in the capillary, the capillary is replaced with a new capillary array.

The capillary is formed of a glass tube with an inner diameter of several tens to several hundreds of microns and an outer diameter of several hundreds of microns, and a surface thereof is coated with polyimide to improve an intensity thereof. However, a light irradiation unit irradiated with laser light has a structure in which a polyimide coating film is removed so that internal light emission easily leaks to the outside. The inside of the capillary 202 is filled with a separation medium for providing a difference in a migration speed during the electrophoresis. The separation medium has both fluidity and non-fluidity, but in the embodiment, a fluid polymer is used.

The detection unit 216 is a member that acquires information depending on the sample. When the detection unit 216 is irradiated with excitation light emitted from a light source 214, fluorescence which is information light and has a wavelength depending on the sample is generated from the sample, and the fluorescence is emitted to the outside. The information light is separated in a wavelength direction by a diffraction grating 232, and the spectroscopic information light is detected by an optical detector 215 and the sample is analyzed.

A capillary cathode side end 227 is fixed through a metallic hollow electrode 226, respectively. A tip of the capillary is in a state of protruding by about 0.5 mm from the hollow electrode 226. All the hollow electrodes equipped for each capillary are integrated and attached to the load header 229. All the hollow electrodes 226 are electrically connected to the high voltage power supply 204 mounted on a main body of the device, and operate as a cathode electrode when it is required to apply a voltage such as electrophoresis, sample introduction, or the like.

An end (the other end) of the capillary on the opposite side of the capillary cathode end side 227 is bundled together by the capillary head 233 into one. The capillary head 233 can be connected to a block 207 in a pressure-resistant airtight manner. The high voltage from the high voltage power supply 204 is applied between the load header 229 and the capillary head 233. Next, a syringe 206 fills the capillary with a new polymer from the other end. Polymer refilling in the capillary is performed to improve measurement performance for each measurement.

The pump mechanism 203 is formed of the syringe 206 and a mechanical system for pressurizing the syringe 206. The block 207 is a connection unit for allowing the syringe 206, the capillary array 217, an anode buffer container 210, and a polymer container 209 to communicate with each other.

An optical detection unit that detects the information light from the sample includes: the light source 214 for irradiating the above-described the detection unit 216; the optical detector 215 for detecting light emission in the detection unit 216; and the diffraction grating 232. When the sample in the capillary separated by the electrophoresis is detected, the detection unit 216 of the capillary is irradiated with the light source 214, the light emitted from the detection unit 216 is separated by the diffraction grating 232, and the separated light is detected by the optical detector 215.

The constant temperature bath 218 is covered with a heat insulating material in order to keep the inside of the constant temperature bath 218 at a constant temperature, and the temperature is controlled by a heating and cooling mechanism 220. A fan 219 circulates and agitates the air in the constant temperature bath 218 to keep the temperature of the capillary array 217 positionally uniform and constant.

The conveyor 225 includes three electric motors and a linear actuator, and can move in three axes in vertical, horizontal, and depth directions. At least one or more containers can be placed on a moving stage 230 of the conveyor 225. The moving stage 230 includes an electric grip 231, thereby making it possible to grab and release each container. Therefore, a buffer container 221, a cleaning container 222, a waste liquid container 223, and a sample plate 224 can be conveyed up to the capillary cathode end 227 as needed. Unnecessary containers are stored in a predetermined storage place in the device.

The electrophoresis device 105 is used in a state of being connected to the data analysis device 112 with a communication cable. An operator can control the functions of the device by the data analysis device 112, and transmit and receive data detected by the detector in the device.

The electrophoresis device 105 may include a sensor for acquiring environmental information that may affect the electrophoresis. As an example, an in-device sensor unit 240, a polymer sensor unit 241, and a buffer solution sensor unit 242 are illustrated in FIG. 2. The in-device sensor unit 240 is a group of sensors for acquiring environmental information in the device, and examples of the environmental information include temperature, humidity, atmospheric pressure, or the like in the device. The polymer sensor unit 241 is a group of sensors for acquiring information on quality of the polymer, and examples thereof include a PH sensor, an electrical conductivity sensor, or the like. While FIG. 2 illustrates an example in which the polymer sensor unit 241 is installed in the polymer container 209, a position of the polymer sensor unit 241 is not limited to this position. The buffer solution sensor unit 242 is a group of sensors for acquiring information on quality of buffer solution, and an example thereof is a temperature sensor. While FIG. 2 illustrates an example in which the buffer solution sensor unit 242 is installed in the anode buffer container 210, a position of the buffer solution sensor unit 242 is not limited to this position. The buffer solution sensor unit 242 may be set in the buffer container 221.

An outline of a process flow of the genotype analysis device and the genotype analysis method according to the present embodiment will be described with reference to FIG. 3. First, an electrophoresis process of an actual sample to be analyzed is performed (step 301, hereinafter S301). Next, in S302, a fluorescence intensity of each fluorescent dye is calculated from spectral waveform data obtained by the electrophoresis. Next, in S303, a peak is detected from the waveform of the fluorescence intensity. Next, in S304, a correspondence relationship between time and a DNA fragment length is obtained by mapping obtained peak time with information on a known DNA fragment length of a size standard. The process is referred to as Size Calling. Next, in S305, an allele is identified from the obtained individual DNA fragment lengths. The process is referred to as Allele Calling.

Figure 4:
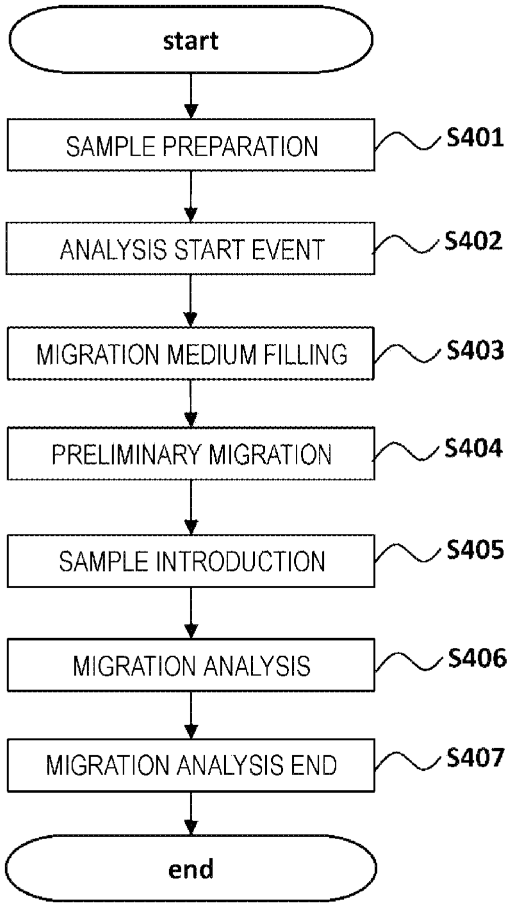
FIG. 4 is a diagram illustrating an electrophoresis process flow according to the first embodiment.

Hereinafter, details of the process in each of the above-described steps will be described with reference to the drawings. FIG. 4 illustrates a flow of the electrophoresis process of the actual sample in S301. A basic procedure of the electrophoresis can be roughly divided into sample preparation (S401), analysis start event (S402), migration medium filling (S403), preliminary migration (S404), sample introduction (S405), and migration analysis (S406).

An operator of the device sets a sample and a reagent in the device as the sample preparation (S401) before the start of analysis. More specifically, first, the buffer container 221 and the anode buffer container 210 are filled with a buffer solution forming a part of an energization path. The buffer solution is, for example, an electrolyte solution commercially available from various companies for electrophoresis. The sample to be analyzed is dispensed into a well of the sample plate 224. The sample is, for example, a PCR product of DNA. A cleaning solution for cleaning the capillary cathode end 227 is dispensed into the cleaning container 222. The cleaning solution is, for example, pure water. The migration medium for performing the electrophoresis of the sample is injected into the syringe 206. Examples of the migration medium include polyacrylamide-based separation gel, a polymer, or the like commercially available from various companies for the electrophoresis. The capillary array 217 is replaced when the capillary 202 is expected to deteriorate, and when the length of the capillary 202 is changed.

At this time, as the sample to be set on the sample plate 224, in addition to the actual sample of DNA to be analyzed, there are positive control, negative control, and an allelic ladder, and electrophoresis is performed in different capillaries. The positive control is, for example, a PCR product containing known DNA, and is a sample for a control experiment to confirm that DNA is correctly amplified by PCR. The negative control is a PCR product not containing DNA, and is a sample for a control experiment to confirm that contamination such as operator DNA, dust, or the like is not generated in a PCR amplification product.

The allelic ladder is an artificial sample containing a large number of alleles that may be generally contained in a DNA marker, and is normally provided by a reagent manufacturer as a reagent kit for the DNA test. The allelic ladder is used to fine-tune a correspondence relationship between the DNA fragment length and the allele in individual DNA markers. The allelic ladder will be described later.

Figure 7A:
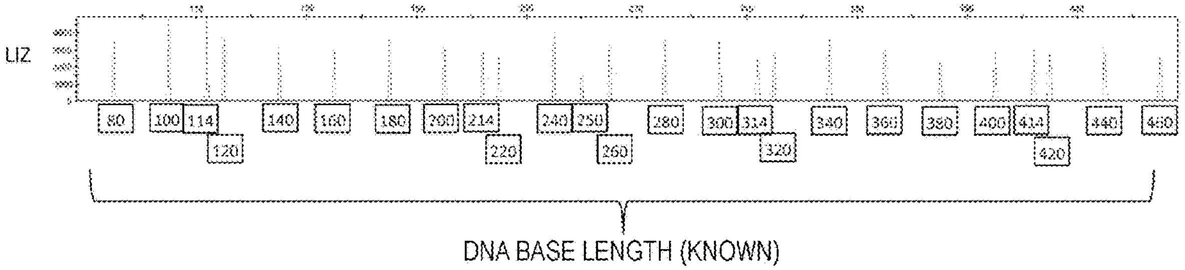
FIGS. 7A and 7B are diagrams illustrating an outline of Size Calling according to the first embodiment.

A known DNA fragment labeled with a specific fluorescent dye referred to as a size standard is mixed with all the samples including the actual sample, the positive control, the negative control, and the allelic ladder. A type of the fluorescent dye allocated to the size standard varies depending on the reagent kit to be used. For example, in a size standard reagent illustrated in FIG. 7A, it is assumed that known DNA fragments having lengths between 80 bp and 480 bp are labeled with fluorescent dye LIZ. The size standard is mixed with all the capillary samples for the purpose of obtaining a correspondence relationship between scan time and the DNA fragment length in Size Calling which will be described later.

The operator specifies a type of allelic ladder, a type of size standard, a type of fluorescent reagent, a type of sample set in the well on the sample plate 224 corresponding to each capillary, or the like. In the present embodiment, any one of the actual sample, the positive control, the negative control, and the allelic ladder is specified as the type of sample. The setting of these pieces of information is set in the sample information setting unit 106 via the user interface unit 103 on the data analysis device 112.

Next, after the sample preparation (S401) as described above is completed, the operator operates the user interface unit 103 on the data analysis device 112, and instructs the start of analysis. The instruction for starting the analysis is transmitted to the electrophoresis device control unit 108. The analysis starts by allowing the electrophoresis device control unit 108 to transmit an analysis start signal to the electrophoresis device 105 (S402).

Next, in the electrophoresis device 105, the migration medium filling (S403) is started. The step may be automatically performed after the analysis starts, and may be performed by allowing the electrophoresis device control unit 108 to sequentially transmit control signals. The migration medium filling is a procedure of filling the capillary 202 with a new migration medium and of forming a migration path.

In the migration medium filling (S403) of the present embodiment, first, the waste liquid container 223 is conveyed directly under the load header 229 by the conveyor 225, and a solenoid valve 213 is closed so that a used migration medium discharged from the capillary cathode end 227 can be received. Next, the syringe 203 is driven to fill the capillary 202 with a new migration medium, and the used migration medium is discarded. Finally, the capillary cathode end 227 is immersed in the cleaning solution in the cleaning container 222, and the capillary cathode end 227 contaminated with the migration medium is washed.

Next, the preliminary migration (S404) is performed. The step may be automatically performed, or may be performed by allowing the electrophoresis device control unit 108 to sequentially transmit control signals. The preliminary migration is a procedure in which a predetermined voltage is applied to the migration medium, and the migration medium is caused to be in a state suitable for electrophoresis. In the preliminary migration (S404) of the present embodiment, first, the capillary cathode end 227 is immersed in the buffer solution in the buffer container 221 by the conveyor 225 to form an energization path. Next, the high voltage power supply 204 applies a voltage of about several to several tens of kilovolts to the migration medium for several to several tens of minutes, such that the migration medium is caused to be in the state suitable for the electrophoresis. Finally, the capillary cathode end 227 is immersed in the cleaning solution in the cleaning container 222, and the capillary cathode end 227 contaminated with the buffer solution is washed.

Next, the sample introduction (S405) is performed. The step may be automatically performed, or may be performed by allowing the electrophoresis device control unit 108 to sequentially transmit control signals. In the sample introduction (S405), a sample component is introduced into the migration path. In the sample introduction (S405) of the present embodiment, first, the conveyor 225 immerses the capillary cathode end 227 in the sample stored in the well of the sample plate 224, and then the solenoid valve 213 is opened. As a result, an energization path is formed, and the sample component can be introduced into the migration path. Next, a pulse voltage is applied to the energization path by the high voltage power supply 204, and the sample component is introduced into the migration path. Finally, the capillary cathode end 227 is immersed in the cleaning solution in the cleaning container 222, and the capillary cathode end 227 contaminated with the sample is washed.

Next, the migration analysis (S406) is performed. The step may be automatically performed, or may be performed by allowing the electrophoresis device control unit 108 to sequentially transmit control signals. In the migration analysis (S406), each sample component contained in the sample is separated and analyzed by electrophoresis. In the migration analysis (S406) of the present embodiment, first, the conveyor 225 immerses the capillary cathode end 227 in the buffer solution in the buffer container 221 to form an energization path. Next, the high voltage power supply 204 applies a high voltage of about 15 kV to the energization path, thereby generating an electric field in the migration path. By the generated electric field, each sample component in the migration path moves to the detection unit 216 at a speed depending on a property of each sample component. That is, the sample components are separated by a difference in movement speeds thereof. Next, the sample components that reach the detection unit 216 are detected in order. For example, when the sample contains a large number of DNAs having different base lengths, a difference in movement speeds is generated depending on the base lengths thereof, and the DNA having the shortest base length reaches the detection unit 216 in order. A fluorescent dye depending on the terminal base sequence of the DNAs is attached to each DNA. When the detection unit 216 is irradiated with the excitation light emitted from the light source 214, information light, that is, fluorescence having a wavelength depending on the sample is generated from the sample, and then emitted to the outside. The information light is detected by the optical detector 215. During the migration analysis, the optical detector 215 detects the information light at regular time intervals, and transmits image data to the data analysis device 112. Alternatively, in order to reduce an information amount to be transmitted thereto, luminance of only a partial area of the image data may be transmitted thereto instead of the image data. For example, a luminance value sampled only at wavelength positions at regular intervals may be transmitted for each capillary. The luminance value data represents a spectral waveform of each capillary. The spectral waveform is stored in the storage unit 104.

Finally, when the planned image data is acquired, the voltage application is stopped and the migration analysis is completed (S407). The above description is an example of the electrophoresis process (S301) in FIG. 3.

Figure 3:
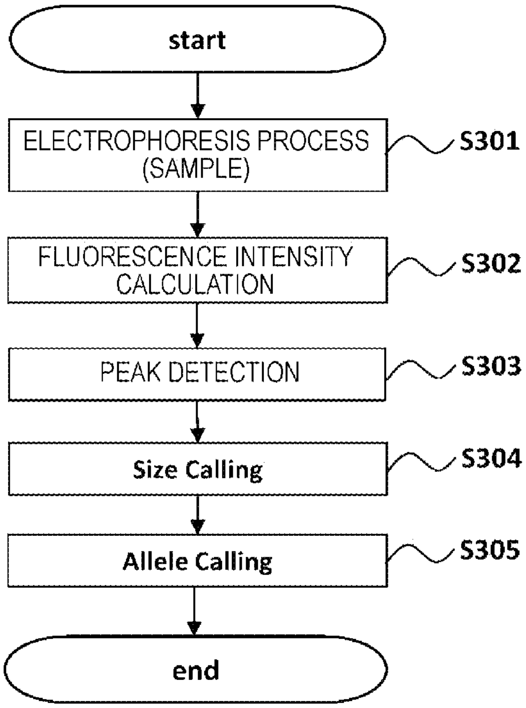
FIG. 3 is a diagram illustrating a process flow of the genotype analysis device according to the first embodiment.

Next, the intensity of each fluorescent dye is calculated from the image data obtained by the electrophoresis process (S301) in FIG. 3 described above (S302). A fluorescence intensity calculation process is performed by the fluorescence intensity calculation unit 110 in FIG. 1. In the fluorescence intensity calculation process (S302), when the spectral waveform data stored in the storage unit 104 in S301 is sampled at λ(0) to λ(19), that is, at 20 wavelength positions, the fluorescence intensity of each dye is calculated by multiplying an intensity ratio of each fluorescent dye and adding the one multiplied by the intensity ratio at each wavelength. When the calculation is represented by a matrix, (Equation 1) is obtained as follows.

[Equation 1]

$$c=Mf$$

$$c=c_F c_V c_N c_P c_L t$$

$$f=f_0 f_1 \ldots f_{18} f_{19} t \qquad \text{Equation 1}$$

In (Equation 1), a vector c is a fluorescence intensity vector, and elements $c_F$, $c_V$, $c_N$, $c_P$, and $c_L$ respectively represent fluorescence intensities of 6FAM, VIC, NED, PET, and LIZ.

A vector f is a measured spectrum vector, and elements $f_0$ to $f_{19}$ respectively represent signal intensities (luminance values) at the wavelengths from λ (0) to λ (19). Alternatively, the elements $f_0$ to $f_{19}$ may be arithmetic mean of the signal intensities in the vicinity of the wavelengths from λ (0) to λ (19), respectively. Measurement signals of individual wavelengths from λ (0) to λ (19) detected by the optical detector 215 include Raman scattered light from the polymer filled in the capillary as a baseline signal in addition to the signal by the fluorescent dye. Therefore, when calculating the vector f, it is necessary to remove the baseline signal in advance.

As an example of a removal method of the baseline signal, the baseline signal may be removed by applying a high-pass filter that removes a low-frequency component with respect to the measurement signals of the respective wavelengths from λ (0) to λ (19). Alternatively, a minimum value in the vicinity of each time may be used as a baseline signal value at that time.

A matrix M is a matrix that converts a measurement spectrum f into the fluorescence intensity vector, and an element thereof corresponds to the intensity ratio of each fluorescent dye at each wavelength. It is indicated that as a value of the intensity ratio is higher, contribution to the intensity of the fluorescent dye at the wavelength is higher.

While the matrix M is originally determined centrally by a type of fluorescent dye and a condition of the migration path, and actually, the matrix M may fluctuate depending on a positional relationship between the capillary and the detector, such that it is necessary to perform calculation when the capillary is replaced. A series of processes for obtaining the matrix M is spectral calibration. The spectral calibration is generally performed by electrophoresis of a sample referred to as a matrix standard. The matrix standard is a reagent for acquiring a fluorescence spectrum and performing the electrophoresis for the purpose of obtaining the above-described matrix.

As described in JP-B-6087128, the matrix may be calculated based upon the migration data of the actual sample to be measured without using the matrix standard. It is assumed that the present embodiment is not limited to the spectral calibration, and the matrix can be obtained in advance.

By using an initial value of the matrix M, the fluorescence intensity of each fluorescent dye is calculated from the measurement spectrum by (Equation 1). Time series data of the fluorescence intensity of each capillary can be obtained by performing the process on the spectrum of each capillary at each time. Hereinafter, the time series data of the fluorescence intensity will be referred to as a fluorescence intensity waveform.

Figure 5:
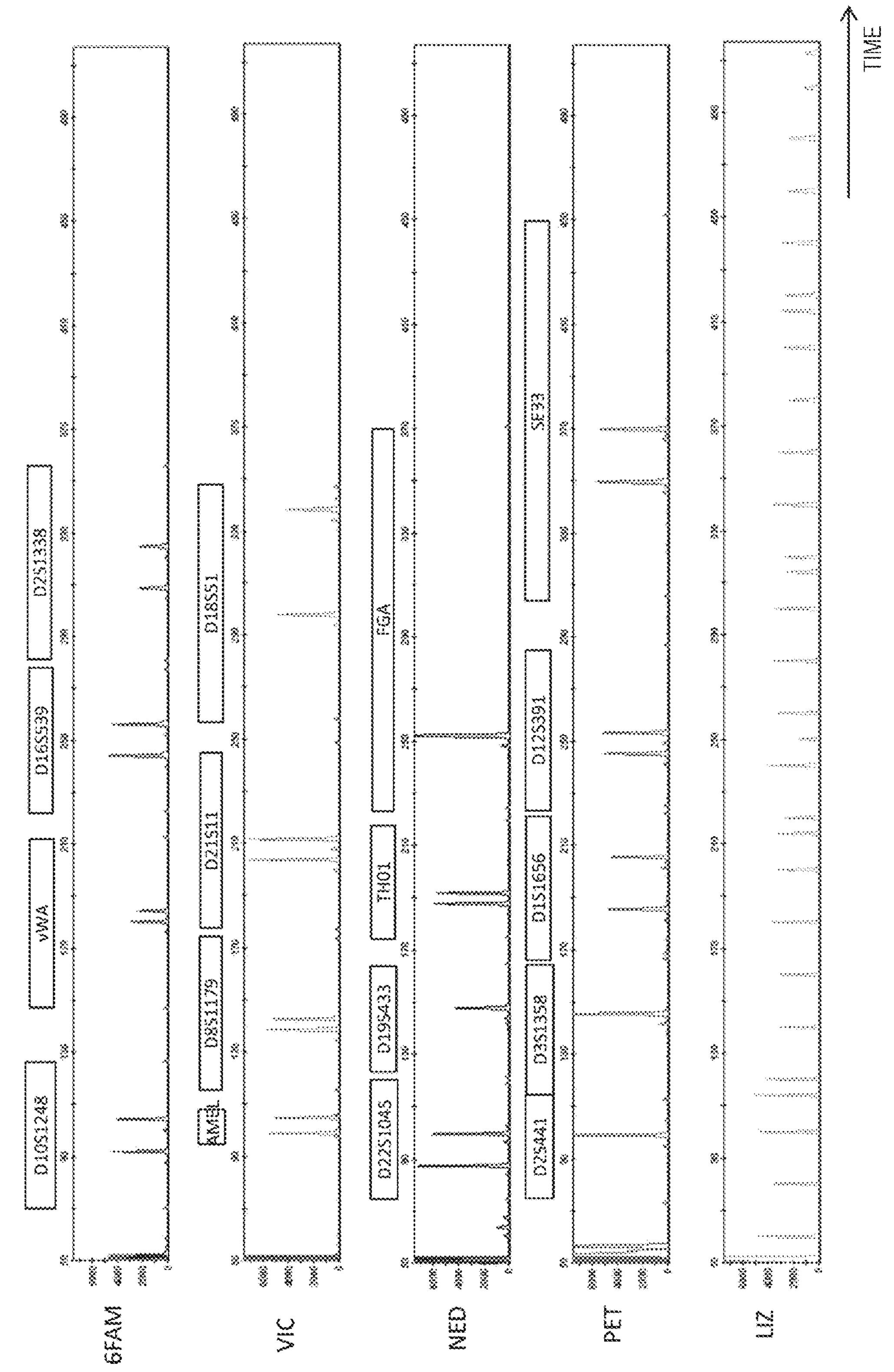
FIG. 5 is a diagram illustrating an example of a fluorescence intensity waveform of an actual sample.

FIG. 5 illustrates an example of the fluorescence intensity waveform of the actual sample obtained in S302 after the electrophoresis (S301). Time at which a peak of each fluorescence intensity stands corresponds to the length of the DNA fragment labeled with each fluorescent dye, and a difference in the lengths corresponds to a difference in the alleles. In the fluorescence intensity waveform of FIG. 5, one or two peaks are included for each DNA marker, and when there is one peak, it can be seen that the fluorescence intensity of the one peak is higher than those of the two markers. When there is one peak, it indicates homozygote (a father-derived allele and a mother-derived allele are the same), and when there are two peaks, it indicates heterozygote (the father-derived allele and the mother-derived allele are different). FIG. 5 illustrates an example in which one person contributes to the DNA of the sample, and when the sample is a mixture of DNAs from a plurality of people, there may be three or more peaks for one DNA marker, depending on a contribution rate of the plurality of people.

Next, peak detection (S303) is performed on the fluorescence intensity waveform obtained by the fluorescence intensity calculation process (S302) in FIG. 3. In the peak detection, a center position (peak time) of the peak, a height of the peak, and a width of the peak are mainly important. The central position of the peak corresponds to the DNA fragment length and is most important for allele identification. The height of the peak is used for identifying the homozygote and the heterozygote, and for quality evaluation such as a level of DNA concentration in the sample. The width of the peak is also important for evaluating quality of the sample and an electrophoresis result. Gaussian fitting, which is a known technology, can be used as one of the methods for estimating a peak parameter of such actual data.

Figure 6:
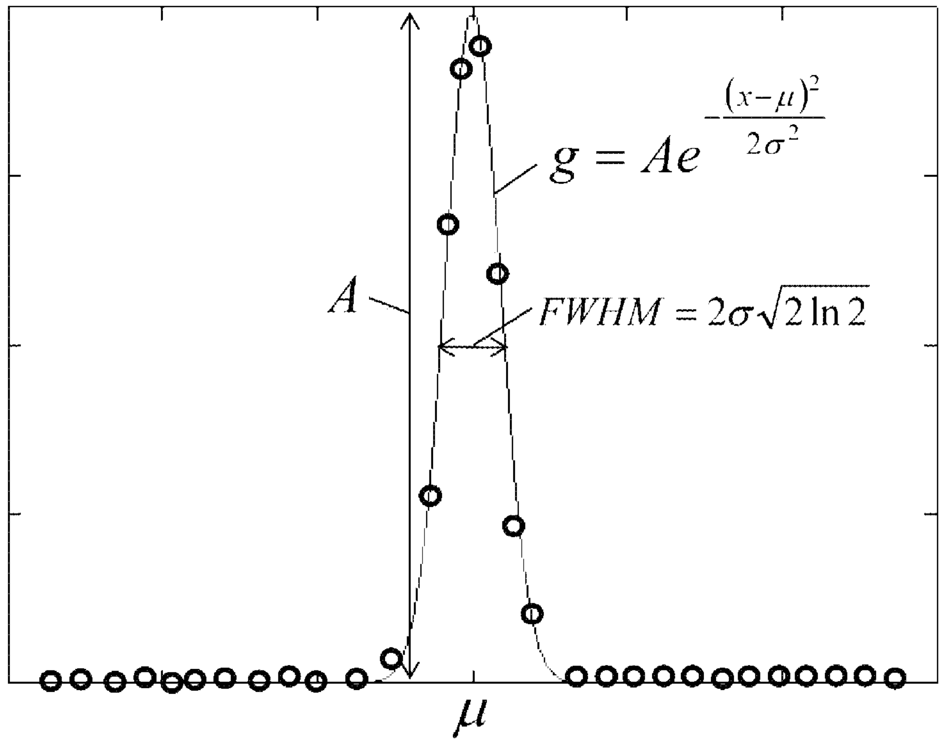
FIG. 6 is a diagram illustrating an outline of Gaussian fitting.

FIG. 6 illustrates a concept of Gaussian fitting. As illustrated in FIG. 6, Gaussian fitting is a process of calculating parameters (a mean value μ, a standard deviation σ, and a maximum amplitude value A) such that a Gaussian function g most approximates the actual data, with respect to the actual data in a certain section. A least squares error between the actual data and a Gaussian function value is often used as an index indicating a degree of approximation of the actual data. As a numerical calculation method that minimizes the least squares error, the parameters can be optimized by using a method of a related art such as a Gauss-Newton method or the like. As disclosed in US-A-2009/0228245A1, a method for improving the accuracy may be applied when two or more peak waveforms are mixed or when data around the peak is asymmetric. When a variance σ of the Gaussian function g is determined, a full width at half maximum (FWHM) can be obtained by an equation shown in FIG. 6. The value can be used as the peak width.

In this manner, the peak parameters are obtained with respect to the fluorescence intensity waveforms of all the fluorescent dyes. At this time, when the peak width and the peak height do not satisfy a predetermined threshold condition, the unsatisfied peak width and peak height may be excluded from the peak.

Next, the Size Calling process (S304) in FIG. 3 is performed. Size Calling is a process of associating the time required for the DNA fragment to be detected by the electrophoresis with the base length of the DNA fragment (hereinafter referred to as a DNA base length). In the present embodiment, Size Calling is performed by the Size Call unit 121 in the STR analysis unit 109 illustrated in FIG. 8 in the data analysis device 112. Specifically, as described above, the electrophoresis is performed on the reagent which contains the DNA fragment having a known length referred to as the size standard and in which the DNA fragment having a known length is labeled with a particular fluorescent dye. For example, in the size standard reagent illustrated in FIG. 7A, the known DNA fragments having lengths between 80 bp and 480 bp are labeled with the fluorescent dye LIZ. The known DNA fragment length is associated with a center position of the peak obtained by the above-described peak detection (S303), that is, the peak time. A known dynamic programming method or the like is used for the association. From a combination of the peak time and the known DNA base length, a relational expression between the electrophoresis time and the DNA base length can be obtained.

Figure 7B:
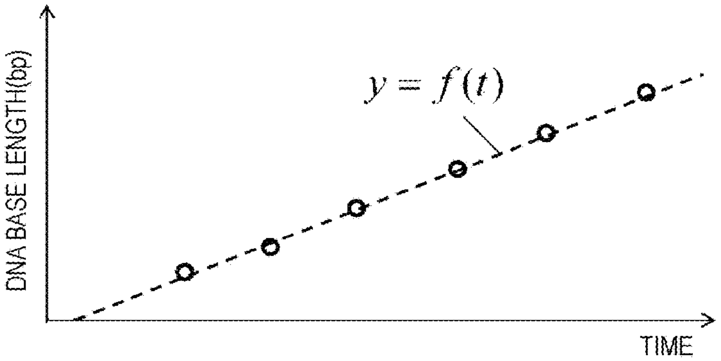

FIG. 7B is a diagram illustrating how a relational expression "y=f (t)" between the DNA migration time (t) and the DNA base length (y) is obtained. The known DNA base length of the size standard and the peak time corresponding thereto are plotted, and the relational expression y=f(t) that most approximates the plot is obtained. As f(t), a quadratic equation, a cubic equation, or the like may be used to perform an approximation that minimizes a square error thereof. A user may specify what kind of approximate expression is used to the STR analysis unit 109 via the user interface unit 103. The relational expression "y=f(t)" between the DNA migration time (t) and the DNA base length (y) obtained in this manner is obtained for all the capillaries, and stored. From the peak time of the fluorescence intensity waveform measured in each capillary, the DNA base length at that time can be obtained by using the relational expression.

Next, the Allele Calling process (S305) illustrated in FIG. 3 is performed. As described above, Allele Calling is a process of identifying the allele from the DNA base length of each peak obtained by the Size Calling process. In the present embodiment, Allele Calling is performed by the mobility model management unit 122 and the Allele Call unit 123 in the STR analysis unit 109 illustrated in FIG. 8 in the data analysis device 112.

Figure 9:
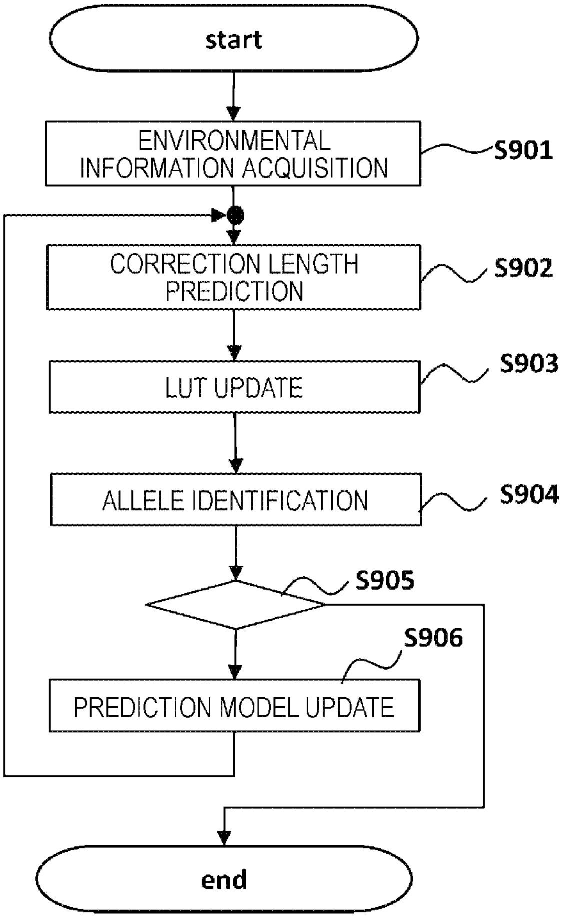
FIG. 9 is a diagram illustrating a process flow of Allele Calling according to the first embodiment.

FIG. 9 is a flowchart illustrating a process flow of the Allele Calling process (S305). The Allele Calling process in the present embodiment is characterized in that environment information acquisition (S901) and correction length prediction (S902) are performed before LUT update (S903) in the same manner as that of a related art.

<LUT Update by Allelic Ladder of Related Art>

In order to show the characteristics of the Allele Calling process of the present embodiment, a process of the LUT update (S903) of the related art in which the processes of S901 and S902 are not performed will be described first. The process of the LUT update of the related art is performed based upon an electrophoresis result of the allelic ladder.

A LUT 113 illustrated as an example in FIG. 10 is used as basic information of the allelic ladder, and includes information such as a Locus name (Locus) labeled by each fluorescent dye (Dye), an allele name (Allele) in the locus, a DNA base length (Length) corresponding to the allele, and an allowable base length width (Min/Max) from a center position of each allele. For example, in FIG. 10, a DNA marker (locus) D10S1248 is labeled with 6FAM, alleles thereof include 8, 9, 10, 11, 12, 13, 14, 15, 16, 17, and 18, and standard DNA base lengths thereof (unit is bp) are respectively 77, 81, 85, 89, 93, 97, 101, 109, 113, and 117. It is shown that all the alleles have a tolerance of plus 0.5 bp and minus 0.5 bp. As described above, it is assumed that the Allele Call unit 123 has the LUT including each allele and the standard DNA base length thereof inside in advance.

However, the standard DNA base length in the LUT 113 is just a standard one, and is generally different from a base length of an allele obtained by actually performing electrophoresis on the sample and measuring the sample. Therefore, usually, an individual allele length is measured by performing electrophoresis on an allelic ladder reagent.

Figure 11:
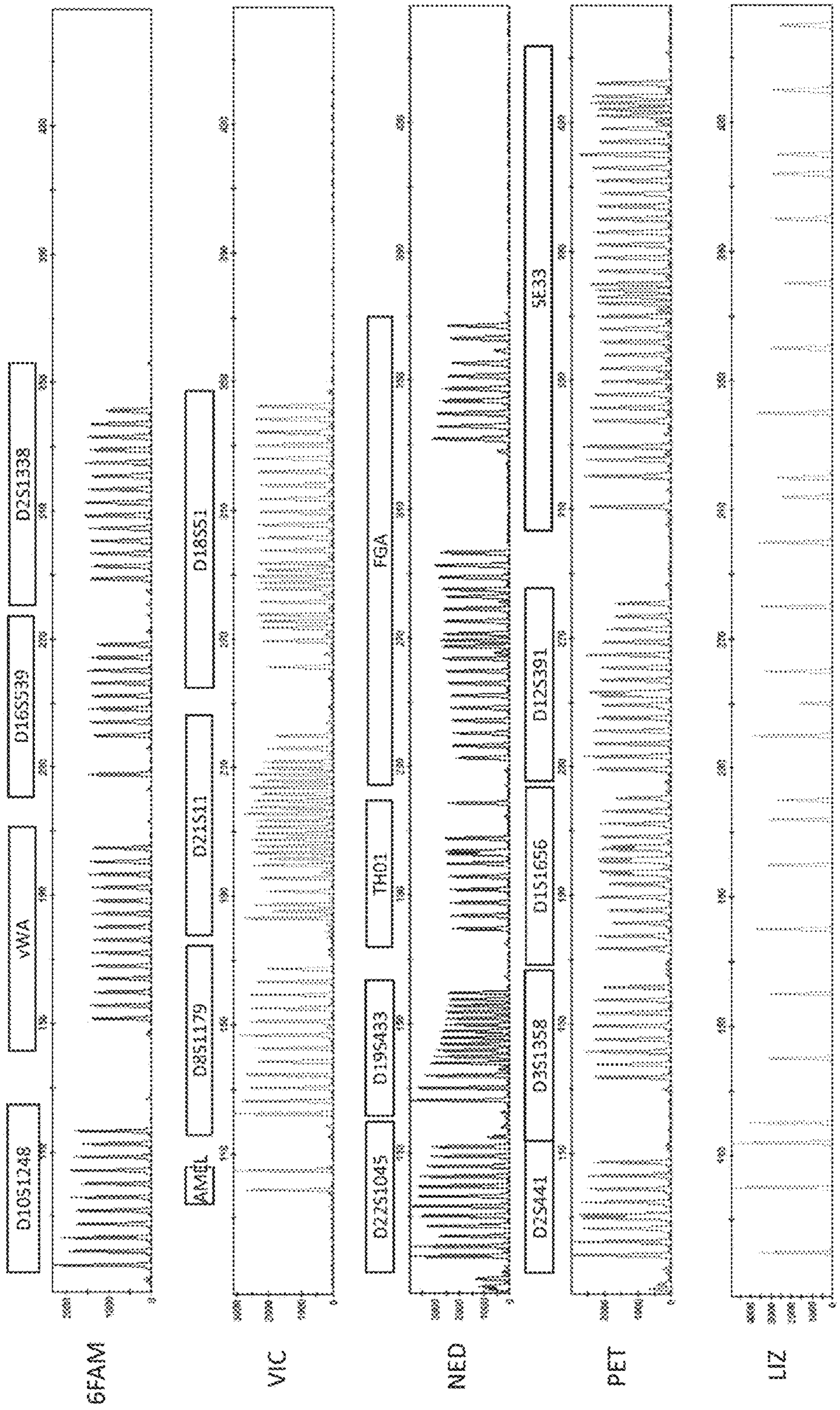
FIG. 11 is a diagram illustrating an example of a fluorescence intensity waveform of an allelic ladder.

FIG. 11 illustrates an example of the fluorescence intensity waveform obtained by the electrophoresis of the allelic ladder. In the waveform, each allele of the DNA marker in each fluorescent dye appears as a peak. The base length of each allele can be obtained by performing the above-described peak detection and Size Calling process on the peak.

Figures 12, 13:
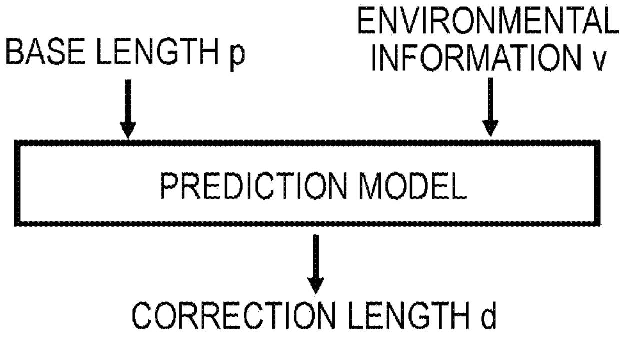
FIG. 12 is a diagram illustrating a first example of LUT update according to the first embodiment.
FIG. 13 is a diagram illustrating a concept of a prediction model according to the first embodiment.

The base length of each allele obtained in this manner is matched with the standard base length of the LUT 113 in FIG. 10, and stored inside as a correction length with respect to the standard base length in addition to the LUT. An example of a LUT to which the correction length is added is illustrated in FIG. 12. A LUT 114 in FIG. 12 shows that the standard base lengths of the alleles 8, 9, 10, 11, 12, 13, 14, 15, 16, 17, and 18 are respectively 77, 81, 85, 89, 93, 97, 101, 109, 113, and 117, and base lengths obtained by adding the respective correction lengths of 1, 1, 1, 1, 1.1, 1.1, 1.1, 1.1, 1.1, 1.2, and 1.2 (an offset column in FIG. 12) are the base lengths of individual alleles to be actually measured.

The above-described matching may be performed by using the known dynamic programming method or the like in the same manner as that of the above-described Size Calling. The detected peak may include occurrences such as noise peak inclusion, a peak detection failure, or the like. A matching algorithm considering the insertion and omission of the peak may be used. As an evaluation function for obtaining an optimum matching, a distance between the standard base length and the base length of each peak, a peak interval, or the like may be used to perform association between each peak and each allele of the allelic ladder.

As described, by performing the electrophoresis on the allelic ladder reagent, it is possible to obtain the length to be corrected at the time of actual measurement as shown in the LUT 114 of FIG. 12, with respect to the standard base length of FIG. 10.

Figure 15:
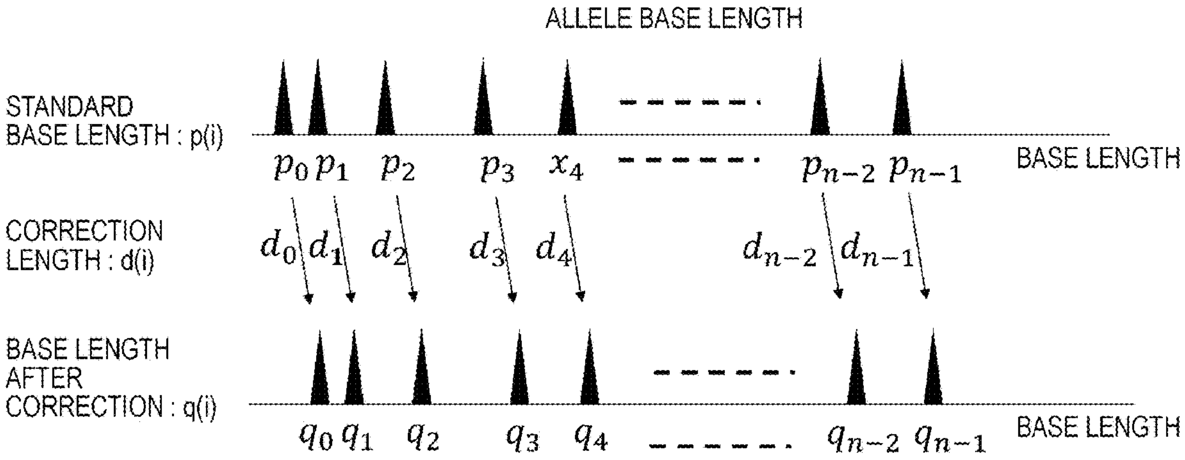
FIG. 15 is a diagram illustrating a concept of allele base length correction according to the first embodiment.

FIG. 15 illustrates a concept of correcting the base length of the allele. As illustrated in FIG. 15, a base length q(i) of the allele to be actually measured (a corrected base length) can be obtained by adding an obtained correction length d(i) to a standard base length p(i) of each allele.

The method for correcting the allele base length using the allelic ladder of the related art is described above. On the other hand, the Allele Calling process of the present embodiment is characterized in that a frequency of using the allelic ladder is reduced, the allelic ladder is not used to reduce running cost for genotypic analysis, and the correction length of the base length of each allele at the time of sample measurement is predicted. Hereinafter, the Allele Calling process of the present embodiment will be described with reference to FIG. 9.

<Environmental Information>

In the Allele Calling process (S305) of the present embodiment, the environmental information acquisition (S901) is performed. The process is performed by the environmental information receiving unit 124. The environmental information receiving unit 124 receives environmental information on a migration condition from the electrophoresis device 105. Here, the environmental information is various information related to electrophoresis that can be observed by the device. Specific examples of the environmental information include: temperature, humidity, pressure in the device that are acquired by the in-device sensor unit 240; temperature of the buffer solution measured by the buffer solution sensor unit 242; electrical conductivity and PH of the polymer measured by the polymer sensor unit 241; a voltage of the high voltage power supply 204; a current value measured by the first ammeter 205 and the second ammeter 212; a frequency of use and the number of days elapsed of the polymer and the buffer solution; a lot number; and information on consumables such as the number of times of use of the capillary.

It is desirable that these pieces of environmental information are information related to characteristics of the electrophoresis. It is desirable to select the environmental information after experimentally observing that the environmental information contributes to improving prediction accuracy of a base correction length which will be described later. However, characteristics of the device fluctuate, such that the environmental information effective for prediction may change. Therefore, as the data to be stored in the device, it is desirable to acquire and store as much environmental information which is presumed to be related to the electrophoresis as possible. It is desirable that what kind of the environmental information is used for the prediction can be changed when a prediction model is generated, as will be described later.

In the following description, as an example of the environmental information, time series data of an environmental temperature and a current to be measured by the second ammeter 212 will be used. However, a disclosed technology according to the present invention is not necessarily limited to these pieces of environmental information, and can be applied to any environmental information available from the device. Such environmental information may be stored in a data file together with the spectral waveform data obtained by the electrophoresis, and may be stored in the storage unit 104.

<Correction Length Prediction Process>

Next, the mobility prediction unit 126 of the mobility model management unit 122 in the present embodiment performs the correction length prediction (S902). As described above, the correction length prediction is a process of predicting the correction length with respect to the standard base length of each allele in the allelic ladder. The correction length prediction process of the present embodiment is different from a related-art technology in that the correction length of each allele is predicted based upon the above-described environmental information. The mobility prediction unit 126 performs the above-described prediction by using the prediction model stored in the prediction model storage unit 125.

FIG. 13 illustrates a concept of the correction length prediction based upon the prediction model in the mobility prediction unit 126. The prediction model is a model that outputs a correction length d at abase length p by inputting a set including a vector v of a value of the environmental information and any base length p. It is known that in the electrophoresis, the migration speed normally tends to increase as the temperature increases and the current value increases. It is known that characteristics of a change in the migration speed are different depending on whether the base length is short or long.

In the present embodiment, it is assumed that a prediction model that reflects such a tendency is generated in advance based upon the measurement of actual data, and then the prediction model is stored in the prediction model storage unit 125. It is assumed that the prediction model is measured by a device manufacturer in advance before the genotype analysis device is shipped, or the prediction model is measured by a service engineer at the time of installing the device and stored in the device. Prediction model information may be added from the outside in response to addition of a reagent, version upgrade, or the like. As described in a second embodiment, it is desirable that the prediction model is generated after learning information based upon the DNA fragment length of each allele obtained by performing actual electrophoresis of the allelic ladder.

The prediction model may be a parametric model in which f can be represented by a form of a specific function when d=f(p, v), and may be a non-parametric model that cannot be represented in the form of the function.

<Parametric Model>

As a simple example as the parametric model, a linear regression model as shown in Equation 2 can be described.

[Equation 2]

$$d=f(p,t,c)=\theta_0+\theta_1 p+\theta_2 t+\theta_3 c \quad \text{Equation 2}$$

In Equation 2, as environmental information v, the model is represented by a parameter θ, in which an environmental temperature at a certain base length x is defined as t and a current value is defined as c. When a set of the input values (p, t, c) is collectively referred to as an input vector x, Equation 2 is represented as follows.

[Equation 3]

$$d=f(x)=\theta_0+\theta_1 x_1+\theta_2 x_2+\theta_3 x_3 \quad \text{Equation 3}$$

Further, expressiveness of the prediction model may be improved by generalizing Equation 3, appropriately defining a basis function $\varphi_k(x)$, and defining Equation 4 as follow.

[Equation 4]

$$d=f(x)=\theta_0+\theta_1\phi_1(x)+\theta_2\phi_2(x)+\theta_3\phi_3(x) \quad \text{Equation 4}$$

Equations 2 to 4 are inputs in which the input vector x and the parameter θ are three-dimensionally expressed, and when the number of elements of the environmental information increases in order to improve the accuracy of prediction, it is also possible to increase dimensions of the input vector x and parameter θ.

<Non-Parametric Model>

Figure 14:
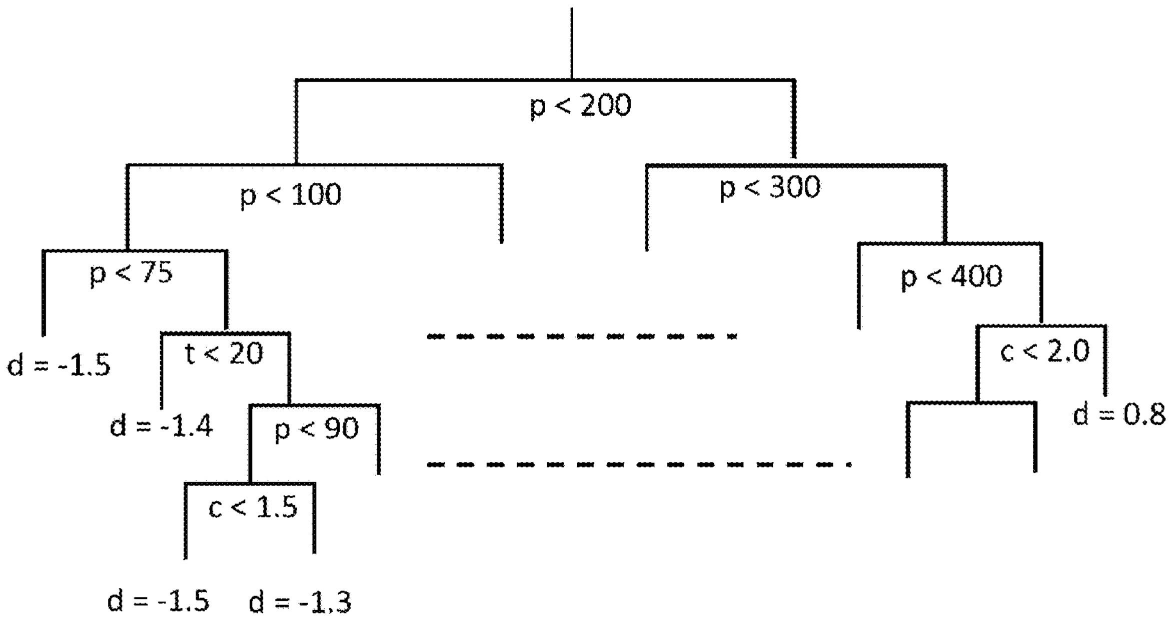
FIG. 14 is a diagram illustrating a concept of a decision tree according to the first embodiment.

The non-parametric model can also be used when appropriate prediction cannot be performed with the parametric model as described above. An example of the non-parametric model includes a known decision tree. That is, an inference rule of a tree structure is used to determine a predicted value with respect to the input vector. FIG. 14 illustrates a conceptual diagram of prediction by the decision tree. As illustrated in FIG. 14, in the decision tree, a base length p, an environmental temperature t, and a current c which are input data start from a root node, and a final predicted value d is determined by a combination of rules as to whether or not a condition in each node is satisfied.

The non-parametric model may be modeled by using known machine learning algorithms such as a random forest that combines the decision trees, a related vector machine (RVM), a neural network.

<Selection of a Plurality of Prediction Models>

The prediction model may not be the only one. A plurality of prediction models may be generated, and the mobility prediction unit 126 may appropriately select the prediction model according to a condition. Hereinafter, items for which it is desirable to use the plurality of prediction models will be described.

It is desirable that the prediction model is generated for each fluorescent dye. The reason is that mobility characteristics of DNA are different depending on the fluorescent dye.

It is desirable that the prediction model is generated for each type of gene analysis panel. The reason is that a type of locus of the allelic ladder and the mobility characteristics of DNA are different depending on the reagent.

It is desirable that the prediction model is generated for each type of polymer. The reason is that the mobility characteristics of DNA are different depending on the type of polymer.

In order to improve the accuracy of the prediction model, the prediction model may be generated for each condition according to the environmental conditions. Examples are described below.

Prediction models to be used depending on different temperature conditions, such as a prediction model to be applied when the environmental temperature is low, a prediction model to be applied when the environment temperature is high, or the like may be prepared.

A prediction model for a high voltage, a prediction model for a low voltage, or the like may be prepared depending on the voltage.

Depending on a frequency of use of the buffer solution, and depending on the number of times of use thereof, a prediction model to be applied when the number of times of use thereof is high, a prediction model to be applied when the number of times of use thereof is low, or the like may be prepared.

A prediction model depending on the number of times of use of consumables such as a capillary or the like and the number of days elapsed thereof may be prepared.

The mobility prediction unit 126 may select an appropriate prediction model from the plurality of prediction models as described above according to an application condition of the prediction model.

Alternatively, a list of applicable prediction models is provided to an operator via the user interface unit 103, and the operator may be able to set priority of the prediction model to be applied from among the list thereof. Alternatively, the list of applicable prediction models is provided to the operator via the user interface unit 103, and the operator may be able to set the priority of the prediction model to be applied from among the list thereof. Alternatively, the list of applicable prediction models is provided to the operator via the user interface unit 103, and the operator may be able to select a model to be applied from among the list thereof.

<LUT Update>

Next, the LUT update process (S903) is performed (FIG. 9). In the LUT update process, the correction length of the base lengths of all the alleles in the LUT obtained in S902 is stored in the LUT. As a data structure of the LUT, as illustrated in FIG. 12, an existing correction length (an Offset column in FIG. 12) may be overwritten. Alternatively, as illustrated in a LUT 115 of FIG. 16, instead of overwriting the existing correction length, the correction length may be newly added and updated while the existing correction length remains as it is.

As described above, in the LUT update process of the related art, the LUT is updated based upon the correction length obtained by actually measuring the allelic ladder, however, in the present embodiment, based upon the environmental information and the base length of each allele, the correction length with respect to the base length of each allele is predicted by using the prediction model, and the LUT is updated based upon the prediction result. Accordingly, it is possible to obtain LUT information close to that at the time of actual sample measurement without using the allelic ladder.

<Allele Identification Process>

Next, an allele identification process (S904) is performed. In the allele identification process, the allele corresponding to each peak is identified from the DNA base length of the peak of the measured actual sample with reference to the LUT whose correction length is determined as described above. That is, as illustrated in FIG. 5, the allele identification process corresponds to identifying which of the alleles in the allelic ladder illustrated in FIG. 11 corresponds to each peak of the fluorescence intensity waveform of the actual sample to be analyzed.

Figures 16, 17:
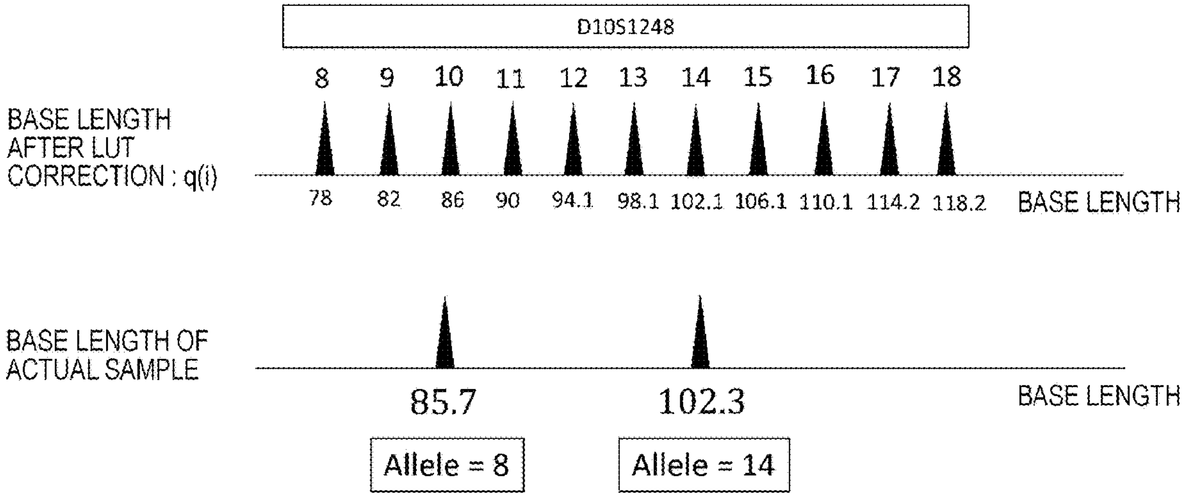
FIG. 16 is a diagram illustrating a second example of the LUT update according to the first embodiment.
FIG. 17 is a diagram illustrating a concept of allele identification according to the first embodiment.

An example of the allele identification process is described with reference to FIG. 17. FIG. 17 illustrates an example of identifying the allele of the locus "D10S1248" labeled with the fluorescent dye 6FAM. An upper part of FIG. 17 illustrates the base lengths of the alleles 8 to 18 in the same locus in the LUT. The base lengths are base lengths after the above-described correction is performed, and in FIG. 17, a numerical value based upon the correction length illustrated in FIG. 12 is described as an example.

At a lower part of FIG. 17, two allele peaks observed in the range of D10S1248 are shown in the actual sample to be analyzed. The base lengths of the two allele peaks are respectively calculated as 85.7 [bp] and 102.3 [bp] by the above-described Sizing Call process.

The Allele Call unit 123 determines which of the respective allele base lengths in the LUT corresponds to the base lengths, and identifies the corresponding alleles. In FIG. 17, the alleles are identified as 8 and 14, respectively. The Allele Call unit 123 identifies the allele of each locus by performing the process as shown in FIG. 17 on all loci of all fluorescent dyes. A combination pattern of the alleles serves as genotype information for personal identification.

As described above, a base length tolerance of each allele is stored in the LUT of FIG. 12 (plus 0.5 bp and minus 0.5 bp in FIG. 12), and an error within the tolerance is allowed to identify the corresponding allele.

<Re-Execution of Correction Value Prediction when Allele Identification Fails>

In S905, it is determined whether or not there is a problem in the allele identification process. When all the alleles are detected within the above-described error tolerance, it is determined that there is no problem and the Allele Calling process is terminated. When there is a DNA marker that does not have a corresponding allele even though the error is allowed with the tolerance, one of the reasons is that the predicted value of the correction length obtained in S902 may not be appropriate. In this case, when there are a plurality of prediction models, another prediction model may be used and the correction length prediction (S902) may be restarted.

In the case of the allele identification failure as described above, a plurality of candidate models and priorities thereof may be automatically determined, or the operator may be able to set the priorities of the respective models via the user interface unit 103.

When the prediction fails in all the candidate prediction models, the correction value calculated by the latest allelic ladder may be applied, or the correction value of the latest successful allele identification process may be applied.

In the prediction model described in the present embodiment, the standard base length of the allele is used as an input, and the correction length to be added to the standard base length of the allele is used as an output. Therefore, in the allele identification process, the correction length is added to the standard base length in the LUT to be associated with the measured allele base length. However, the correction length may be subtracted from the base length of the measured allele to be associated with the standard base length in the LUT. That is, since the correction length in the present invention is fundamentally a difference between the standard base length and the base length to be measured, the correction method using the difference therebetween is the same regardless of whether to use the former or the latter.

The fundamental purpose of the prediction model described in the present embodiment is to obtain a correspondence between the standard base length of the allele and the base length of each allele to be measured. Therefore, the output of the prediction model for obtaining the correspondence therebetween is not limited to the correction length added to the standard base length in the above-described LUT. For example, the output of the prediction model may be a direct value of the base length to be measured instead of the above-described correction length. An example of another prediction model may include a model in which the base length to be measured is inputted and the correction length for predicting the standard base length in the LUT is outputted, and may include a model in which the standard base length in the LUT is directly outputted instead of the correction value. It is easy for the identification process to obtain the correspondence between the standard base length and the measured base length according to an output content of the prediction model as described above.

As described above, in the first embodiment, the correction length of the standard base length in the allelic ladder is predicted based upon the environmental information at the time of using the device, and then the base length of each allele is finely corrected. By the above-described method, the base length of each allele can be finely corrected at the same time as the electrophoresis of the actual sample without performing the electrophoresis using the allelic ladder, such that it is possible to reduce the analysis cost by reducing the frequency of use of the allelic ladder.

Second Embodiment

A genotype analysis device according to a second embodiment will be described. The present embodiment is an embodiment of a genotype analysis device or the like in which a mobility model management unit uses an electrophoresis result of a sample containing DNA having a known standard base length as a data set, and generates a prediction model to be used for prediction by learning from the data set.

In the genotype analysis device according to the first embodiment, the prediction model suitable for a condition of an analysis environment is selected from among the prediction models stored in advance in the prediction model storage unit 125, and the base length of each allele is corrected. In the first embodiment, it is assumed that the prediction model is measured by the device manufacturer in advance before the genotype analysis device is shipped, or is measured by the service engineer when the device is installed and stored in the device.

However, when the electrophoresis characteristics of the device fluctuate more than expected, or when the analysis environment changes by the addition of a new reagent or the like, it is conceivable that the prediction model stored in advance cannot follow the change in environment, such that the correction length prediction of the allele cannot be accurately performed.

In this case, as described in the first embodiment, it is necessary to update the LUT of the related art using the allelic ladder, and there is a problem that the frequency of using the allelic ladder increases.

Therefore, in the second embodiment, the electrophoresis results when the allelic ladder is measured are stored, and the electrophoresis results are used as training data to update the prediction model. Hereinafter, the second embodiment of the present invention will be described in detail with reference to the drawings.

Figure 18:
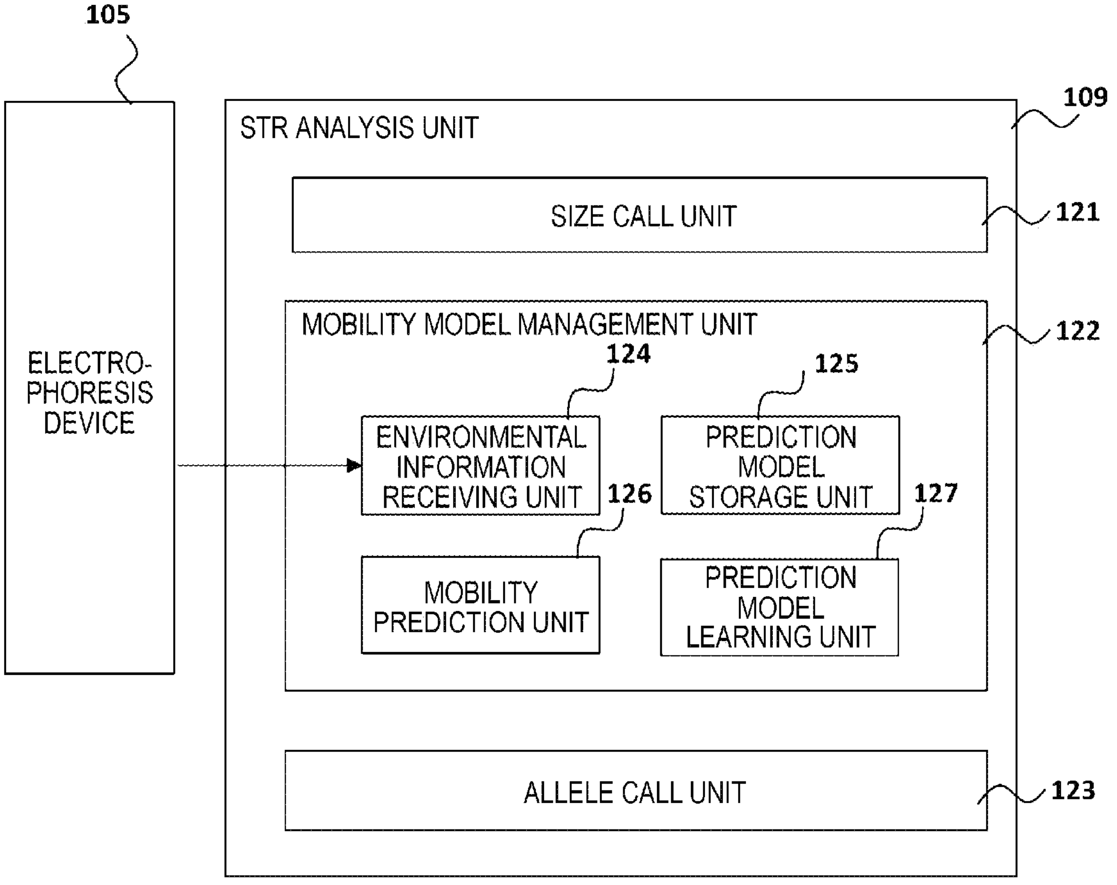
FIG. 18 is a diagram illustrating a schematic configuration of an STR analysis unit according to a second embodiment.

FIG. 18 illustrates a configuration of the genotype analysis device according to the second embodiment. In FIG. 18, in addition to the configuration of the first embodiment illustrated in FIG. 1, a prediction model learning unit 127 is added. Other configurations of FIG. 18 are the same as those of the first embodiment.

Figure 19:
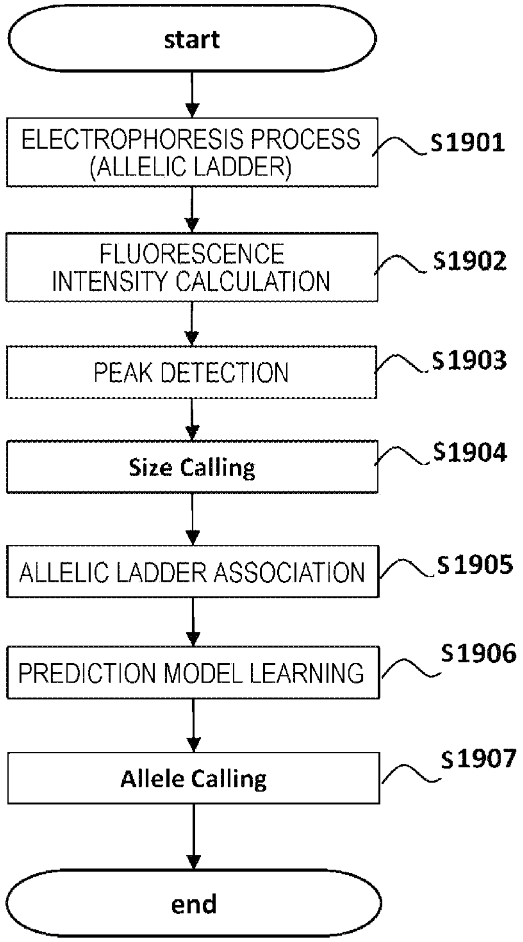
FIG. 19 is a diagram illustrating a process flow of a genotype analysis device according to the second embodiment.

FIG. 19 is a diagram illustrating a process flow of a process of learning a prediction model in the second embodiment. In the learning of the prediction model, an electrophoresis process of the allelic ladder is performed (S1901). A difference from the electrophoresis process (S301) in FIG. 3 is only the difference in the sample to be measured, and the process is the same, so the description thereof will be omitted. The electrophoresis process of the allelic ladder (S1901) and the electrophoresis process of the actual sample (S301) illustrated in FIG. 3 may be performed simultaneously by using different capillaries.

After that, fluorescence intensity calculation (S1902), peak detection (S1903), and Size Calling (S1904) are performed. Since the processes thereof are respectively the same as those of the fluorescence intensity calculation (S302), the peak detection (S303), and the Size Calling (S304) in FIG. 3, the description thereof will be omitted.

Next, the allelic ladder association (S1905) is performed. The association process performs association between the base length sequence of each peak obtained by the Size Calling (S1904) and the standard base length sequence of the allelic ladder. In the same manner as that of the above-described Size Calling, the association process can be performed by using the known dynamic programming method or the like. Since the detected peak may include occurrences such as noise peak inclusion, a peak detection failure, or the like, a matching algorithm considering insertion and omission of the peak may be used. As an evaluation function for obtaining an optimum matching, a distance between the standard base length and the base length of each peak, a peak interval, or the like may be used to perform association between each peak and each allele of the allelic ladder. In this manner, each peak is associated with each allele of the allelic ladder.

Figure 20:
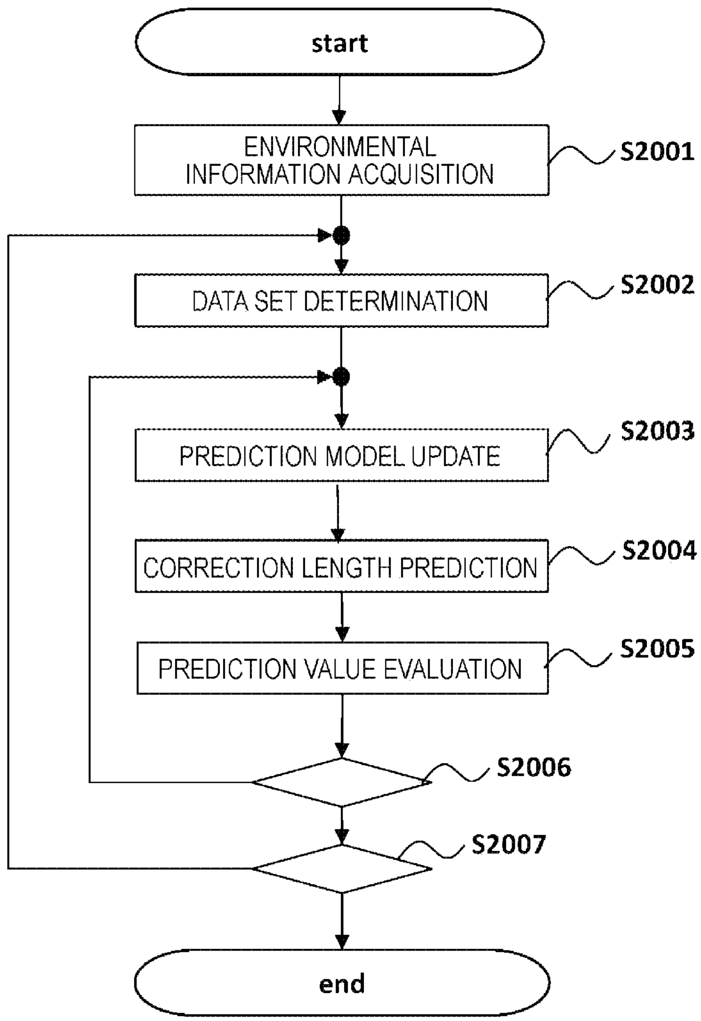
FIG. 20 is a diagram illustrating a process flow of prediction model learning according to the second embodiment.

In this manner, the actual measured values of the base lengths of all the alleles can be obtained from the fluorescence waveform of the allelic ladder. Next, prediction model learning (S1906) is performed. FIG. 20 illustrates a process flow of the prediction model learning. Hereinafter, the prediction model learning in the present embodiment will be described with reference to FIG. 20.

Environmental information acquisition (S2001) is the same as that of S901 in FIG. 9. The environmental information is various information related to electrophoresis performance that can be observed by the device when the electrophoresis of the allelic ladder is performed. The pieces of environmental information are used as input data for the subsequent prediction models.

Figure 21:
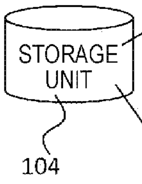
FIG. 21 is a diagram illustrating a concept of a learning data set according to the second embodiment.

Next, a data set to be used for learning is determined (S2002). For learning, the electrophoresis result of the allelic ladder is used. In the present embodiment, it is assumed that data obtained by the electrophoresis of the past allelic ladder is stored in the storage unit 104 as a set with the environmental information. FIG. 21 illustrates a concept of a data set 118 of the allelic latter stored therein. The data set 118 is stored in the storage unit 104, and the data is added each time the electrophoresis of the allelic ladder is performed. However, old data may be deleted according to a capacity of the storage unit 104.

The data set 118 includes at least information on the measurement date and time, a standard base length (Length) of each allele, a correction length (Offset) obtained from a measurement result of each allele, and environmental information used to input prediction. In FIG. 21, an environmental temperature (Temp.) and a current value (Current) are recorded as examples of the environmental information. The data set to be used for learning of the prediction model is determined from among the data set thereof.

In determining the data set of learning, various selection conditions can be considered based upon conditions under which the prediction model to be applied is generated. As an example, the selection conditions for the plurality of models described above are shown.

<Selection Conditions of Data Set for Prediction Model Learning>

It is desirable to divide the data set for each fluorescent dye. The reason is that the mobility characteristics of DNA are different depending on the fluorescent dye.

It is desirable to divide the data set for each type of genetic analysis panel. The reason is that a type of locus of the allelic ladder and the mobility characteristics of DNA are different depending on a reagent.

It is desirable to divide the data set for each type of polymer. The reason is that the mobility characteristics of DNA are different depending on the type of polymer.

The data set may be divided depending on temperature conditions such as a data set when the environmental temperature is low, a data set when the environmental temperature is high, or the like.

The data set may be divided depending on voltage conditions such as a data set when a voltage is high, a data set when a voltage is low, or the like.

The data set may be divided depending on a frequency of use of the buffer solution, the number of times of use thereof, or the like.

The data sets may be divided depending on the number of times of use of consumables such as a capillary or the like and the number of days elapsed thereof.

The respective data sets selected as described above are divided into training data of the prediction model and test data to be used for evaluating prediction accuracy.

Next, a prediction model update process is performed (S2003). The prediction model update uses a training data set to optimize a prediction model parameter.

The prediction model update process varies depending on what kind of prediction model is used. For example, as an example of a parametric model, a known least squares method, parameter estimation by ridge regression, or the like can be applied to a linear regression model as shown in Equation 4.

As a non-parametric model, a known classification and regression trees (CART) algorithm is widely used as an algorithm for learning the tree structure of the decision tree as illustrated in FIG. 14. Known machine learning algorithms such as a random forest, a related vector machine, a neural network, or the like can be applied, thereby making it possible to optimize the prediction model parameter.

Next, the correction length prediction is performed by using the prediction model obtained in S2003 (S2004). The correction length prediction is performed on a test data set determined in S2002. That is, the correction value is predicted by using an input vector in the test data set (the standard base length, the temperature, the current value in the example of FIG. 21) as an input. Since the method of the prediction process is the same as the correction length prediction (S902) described in FIG. 9 of the first embodiment, the description thereof will be omitted.

Next, evaluation of a predicted value obtained in S2004 is performed (S2005). In the evaluation of the predicted value, a difference from the correction value (an offset column in FIG. 21) measured in the test data set is compared. A mean square error is generally used as an index of the difference. A maximum value, a minimum value, a median value, a variance, or the like of the difference may be added as the index.

Next, in S2006, it is determined whether or not to perform the prediction model update. Based upon an evaluation index obtained in S2005, when a predetermined determination condition is not satisfied, a learning parameter in S2003 is changed and learning of the same data set is performed. The learning parameter is a parameter related to an operation of the learning of S2003, such as a learning coefficient when convergence calculation is performed, a constraint condition imposed on the parameter, a learning termination condition, definition of a loss function at the time of learning evaluation, or the like. The learning parameter having the best evaluation index and the prediction model parameter may be selected from a predetermined learning parameter set.

Next, in S2007, it is determined whether or not to change the data set and relearn. When the evaluation index satisfies a predetermined pass level, the satisfied evaluation index is adopted as the prediction model. When the evaluation index does not satisfy the predetermined pass level, the process returns to S2002, and the training data set and the test data set may be divided again and relearned. Data under a specific condition may be deleted from the data set determined in S2002. Data of a new condition may be added to the data set from the data set 118.

The new prediction model obtained as described above can be stored in the prediction model storage unit 125 and used for Allele Calling (S305) with respect to the actual sample as described in the first embodiment.

In the present embodiment, FIG. 19 illustrates an example in which the latest electrophoresis characteristics are reflected by performing learning of the prediction model when the electrophoresis of the allelic ladder is newly performed. However, the timing for performing the learning of the prediction model is not necessarily required to be when the electrophoresis of the allelic ladder is performed. When the storage unit 104 stores a sufficient amount of data set for the learning of the prediction model, the prediction model can be relearned at any timing by some event. As an example of such an event, in the Allele Calling process of the first embodiment, when the allele identification cannot be performed even though the existing prediction model is used, a process of automatically regenerating the prediction model may be performed. Alternatively, an operator may perform an operation of generating a prediction model based upon a new condition via the user interface unit 103.

Allele Calling (S1907) is performed by using the prediction model obtained in this manner. Since the process is the same as Allele Calling (S305) of the first embodiment, the description thereof will be omitted.

As described above, in the genotype analysis device according to the second embodiment of the present invention, it is possible to appropriately learn the prediction model for predicting the base correction length of the allele by using the electrophoresis result of the allelic ladder. As a result, the prediction model is updated by reflecting electrophoresis characteristics of the new allelic ladder, such that the prediction accuracy of the base length of the allele can be maintained and improved, thereby making it possible to reduce the frequency of subsequent use of the allelic ladder and reduce the analysis cost.

Third Embodiment

A genotype analysis device according to a third embodiment will be described with reference to FIGS. 22 and 23. The present embodiment is an embodiment of a genotype analysis device or the like in which when predicting a correspondence, a mobility model management unit evaluates the accuracy of prediction by referring to a base length obtained by electrophoresis of an actual sample that always contains DNA having a known standard base length.

In the genotype analysis device according to the first and second embodiments, the prediction model generated by using the electrophoresis result of the allelic ladder is used, the correction length of the base length of each allele is predicted when the electrophoresis of the actual sample is performed, and the base length of the allele is finely adjusted. When the allele identification fails, another prediction model can be used, or a prediction model can be generated under a new condition.

However, in the first and second embodiments, when the failure of the allele identification cannot be detected, the failure of prediction cannot be detected, and the prediction model cannot be changed or newly added. When the prediction model is significantly inappropriate, a false allele may be identified and the failure of the allele identification may not be detected. Therefore, the third embodiment is characterized in that the accuracy of the prediction model is evaluated by referring to a well-known base length marker in the actual sample.

Hereinafter, the details of the genotype analysis device according to the third embodiment will be described with reference to the drawings. A configuration of the genotype analysis device according to the third embodiment is the same as the configuration illustrated in FIG. 1. A configuration of the STR analysis unit 109 is the same as that of either FIG. 8 or FIG. 18.

In the third embodiment, when a marker having a known base length is included at the time of performing the actual sample measurement, the prediction accuracy is evaluated by referring to the base length of the known marker. Positive control is an example of such a known marker. As described above, when the actual sample is analyzed, in addition to the DNA sample to be analyzed, electrophoresis of the positive control is often performed in different capillaries. The positive control is a PCR product containing DNA having a known base length, and is a sample for a control experiment for confirming that PCR is being correctly performed. Therefore, it is possible to evaluate whether prediction of the correction length is correctly performed by confirming whether the base length of the known DNA marker of the positive control is correctly measured.

In the third embodiment, it is assumed that base length information of the positive control to be used for prediction evaluation of the correction length is stored in the mobility prediction unit 126 in advance before electrophoresis. An example of positive control information is illustrated in FIGS. 23A and 23B.

The positive control information includes at least a fluorescent dye (Dye) and a standard base length (Length) as illustrated in FIG. 23A. The positive control information may also include an error tolerance (Min/Max). The pieces of information may be inputted by an operator through the user interface unit 103, or may be transmitted to the STR analysis unit 109 as a setting file in accordance with a predetermined format. The positive control information once set may be named as setting information and stored in the storage unit 104. Next, when using the positive control, the operator may be able to specify and call the setting information stored in the storage unit 104.

Figure 22:
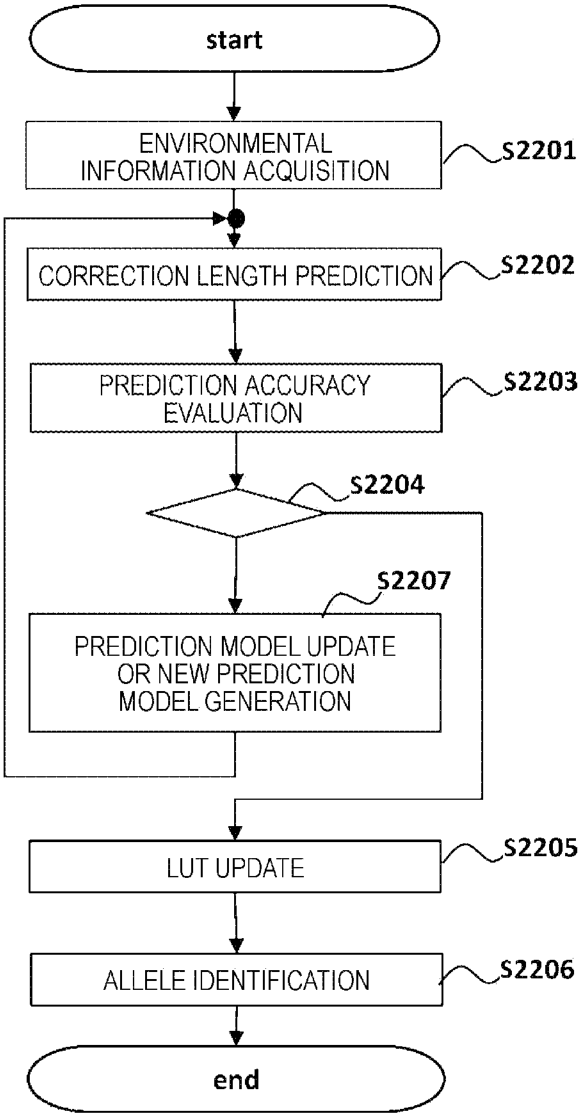
FIG. 22 is a diagram illustrating a process flow of Allele Calling according to a third embodiment.

FIG. 22 is a flowchart of the process of Allele Calling (S305) with respect to the electrophoresis result performed on the actual sample in the third embodiment. Since environmental information acquisition (S2201) is the same as the environmental information acquisition (S901) in the first embodiment, the description thereof will be omitted.

In correction length prediction (S2202), in addition to the correction length prediction (S902) in the first embodiment, as illustrated in positive control information 116 of FIG. 23A, the environmental information at the time of electrophoresis and the standard base length of each known marker are inputted from preset positive control information, and the correction length of the standard base length of the known marker is predicted. A process of the correction length prediction is the same as those of S2202 and S902.

The correction length of each known marker obtained is stored with respect to each marker of the positive control information as illustrated in the positive control information 117 of FIG. 23B (Offset of the positive control information 117). That is, in the correction length prediction (S2202) in the third embodiment, in addition to the prediction of the correction length of the base length of all the alleles stored in the LUT described in the first embodiment (S902), the correction length of the base length of the known marker of the positive control is also predicted.

Next, prediction accuracy evaluation (S2203) is performed. In the process, the base length of each marker measured by electrophoresis of the positive control is associated with the base length of the corrected known marker obtained in S2202, and a difference therebetween is calculated. In the above-described association, the base lengths closest to each other may be used, or a matching technology such as the known dynamic programming method or the like may be used.

In S2204, when the difference with respect to all the known markers is equal to or less than a preset tolerance, it is determined that there is no problem with the prediction accuracy, and then the process proceeds to subsequent LUT update (S2205) and allele identification (S2206). Since the LUT update (S2204) and the allele identification (S2205) are the same as the processes illustrated in FIG. 9 in the first embodiment, the description thereof will be omitted.

In S2204, when the difference with respect to any one of all the known markers is equal to or greater than the preset tolerance, it is determined that there is a problem with the prediction accuracy, and the process proceeds to S2207. In S2207, the prediction model may be changed as described in the first embodiment, or as described in the second embodiment, a prediction model may be generated under a new condition. After S2207, the process starts over from the correction length prediction (S2202).

As described above, in the genotype analysis device according to the third embodiment of the present invention, the prediction accuracy of the correction amount of the base length can be evaluated by referring to the DNA marker having the known base length, which is measured simultaneously with the actual sample. Accordingly, since the prediction accuracy of the base length can be evaluated at the time of measuring the actual sample without using the allelic ladder, it is possible to reduce a risk of an allele determination error when the frequency of use of the allelic ladder is reduced.

While desirable embodiments for performing the present invention have been described above, the present invention is not limited to the embodiments, and is allowed to be appropriately modified within the scope of the gist of the present invention. For example, a microchip-type electrophoresis device in which a sample flow path is formed may be used. In this case, the capillary in this specification may be replaced as the flow path. The present invention can be similarly applied to an electrophoresis device using slab gel.

The present invention can also be implemented by a software program code that implements the functions of the embodiments. In this case, a storage medium on which the program code is recorded is provided to a system or a device, and a computer (or a CPU and an MPU) of the system or the device reads the program code stored in the storage medium. In this case, the program code itself read from the storage medium performs the functions of the above-described embodiments, such that the program code itself and the storage medium in which the program code is stored form the present invention. As the storage medium for supplying the above-described program code, for example, a flexible disk, a CD-ROM, a DVD-ROM, a hard disk, an optical disk, a magneto-optical disk, a CD-R, a magnetic tape, a non-volatile memory card, a ROM, or the like are used.

Based upon an instruction of the program code, an OS (operating system) running on the computer performs a part or all of the actual processes, and the functions of the above-described embodiments may be implemented by the processes. After the program code read from the storage medium is written into the memory on the computer, the CPU or the like of the computer perform a part or all of the actual processes based upon the instruction of the program code, and the functions of the above-described embodiments may be implemented by the processes.

A program code of software implementing the functions of the embodiments may be distributed via a network, the program code thereof may be stored in a storage unit such as a hard disk, a memory, or the like of a system or a device or a storage medium such as a CD-RW, a CD-R, or the like, and at the time of use, the computer (or the CPU and the MPU) of the system or the device may read and execute the program code stored in the storage unit or the storage medium.

What is claimed is:

1. A genotype analysis device for improving prediction accuracy of a base correction length, the genotype analysis device comprising:

an electrophoresis device that implements an electrophoresis comprising environmental information and that determines a spectrum by the electrophoresis; and a data analysis device that determines a measured base length of deoxyribonucleic acid (DNA) based upon the spectrum and that analyzes a genotype with reference to a standard base length, wherein the data analysis device includes a mobility model management unit that predicts a correspondence between the standard base length and the measured base length of the DNA based upon the spectrum and the environmental information in the electrophoresis, wherein the mobility model management unit:

generates a plurality of prediction models that improve the prediction accuracy by utilizing an electrophoresis result of a DNA sample with the standard base length and by learning from a data set comprising the electrophoresis result and the environmental information during the electrophoresis, stores the plurality of prediction models, and selects a first prediction model from the plurality of prediction models by comparing first environmental conditions derived from environmental data and second environmental conditions under which a training dataset for the first prediction model was collected, and according to an environmental condition based upon the environmental information when predicting the correspondence therebetween, wherein the DNA sample comprises a marker comprising a known base length that is utilized when the measured base length is determined, and wherein the prediction accuracy is evaluated by referring to the marker.

2. The genotype analysis device according to claim 1, wherein the mobility model management unit stores a plurality of prediction models to be used for the prediction, and applies the first prediction model in a predetermined priority order when predicting the correspondence therebetween.

3. The genotype analysis device according to claim 1, wherein the data analysis device includes a user interface unit, and wherein the data analysis device displays a list of applicable prediction models on the user interface unit.

4. The genotype analysis device according to claim 1, wherein the mobility model management unit selects the data set according to an environmental condition based upon the environmental information, and learns from a selected data set to generate the plurality of prediction models.

5. The genotype analysis device according to claim 1, wherein the mobility model management unit evaluates accuracy of the prediction by referring to a base length obtained by electrophoresis of an actual sample that always contains DNA whose standard base length is known, when predicting the correspondence therebetween.

6. The genotype analysis device according to claim 5, wherein the mobility model management unit changes the first prediction model or newly learns another prediction model according to an evaluation result of the accuracy of the prediction.

7. The genotype analysis device according to claim 1, wherein an output of the first prediction model comprises a direct value of the base correction length.

8. The genotype analysis device according to claim 1, wherein an output of the first prediction model comprises a correction length for predicting the measured base length.

9. The genotype analysis device according to claim 1, wherein the environmental information includes fluorescence intensity of each fluorescent dye calculated from multiplying an intensity ratio of each fluorescent dye.

10. The genotype analysis device according to claim 1, wherein the first prediction model is a parametric model.

11. The genotype analysis device according to claim 1, wherein the first prediction model is generated for each fluorescent dye based on mobility characteristics of DNA that differ depending on the fluorescent dye.

12. The genotype analysis device according to claim 1, wherein the mobility model management unit divides a training data set and a test data set again and relearns the first prediction model when an evaluation index does not satisfy a predetermined pass level.

13. The genotype analysis device according to claim 1, wherein the marker comprising the known base length is a positive control containing DNA having a known base length for confirming that a polymerase chain reaction (PCR) is correctly performed.

14. The genotype analysis device according to claim 1, wherein the environmental information comprises at least one of temperature, current value, polymer characteristics, or buffer solution characteristics during the electrophoresis.

15. The genotype analysis device according to claim 1, wherein the first prediction model is specifically configured for predicting a correspondence between the standard base length and the measured base length of DNA alleles in an allelic ladder.

16. The genotype analysis device according to claim 1, wherein the environmental information includes electrophoresis-specific parameters comprising at least one of temperature, current value, polymer characteristics, or buffer solution characteristics that affect DNA migration speed during the electrophoresis.

17. A genotype analysis method implemented by genotype analysis device comprising at least one processor coupled to a memory, the genotype analysis method for improving prediction accuracy of a base correction length, the genotype analysis method comprising:

implementing, by an electrophoresis unit of the genotype analysis device, an electrophoresis comprising environmental information to determine a spectrum;

determining, by a data analysis device of the genotype analysis device, a measured base length of deoxyribonucleic acid (DNA) based upon the spectrum;

analyzing, by the genotype analysis device, a genotype with reference to a standard base length;

outputting, by a mobility model management unit of the data analysis device, a correspondence prediction between the standard base length and the measured base length of the DNA based upon the spectrum and the environmental information in the electrophoresis; and generating, by the mobility model management unit, a plurality of prediction models that improve the prediction accuracy by:

utilizing an electrophoresis result of a DNA sample with the standard base length and learning from a data set comprising the electrophoresis result and the environmental information during the electrophoresis, wherein the mobility model management unit stores the plurality of prediction models, and wherein the mobility model management unit selects a first prediction model from the plurality of prediction models by comparing first environmental conditions derived from environmental data and second environmental conditions under which a training dataset for the first prediction model was collected, and according to an environmental condition based upon the environmental information when predicting the correspondence therebetween, wherein the DNA sample comprises a marker comprising a known base length that is utilized when the measured base length is determined, and wherein the prediction accuracy is evaluated by referring to the marker.

* * * * *